(12) United States Patent
Horton et al.

(10) Patent No.: US 11,694,799 B2
(45) Date of Patent: Jul. 4, 2023

(54) SYSTEM AND METHOD FOR DATA INTERROGATION AND/OR REMOTE PROGRAMMING OF A MEDICAL DEVICE

(71) Applicant: BIOTRONIK SE & Co. KG, Berlin (DE)

(72) Inventors: James Horton, Portland, OR (US); Lauren Kraiter, Tigard, OR (US); Dean Bergstrom, West Linn, OR (US); Yarisa Jaroch Gonzalez, West Linn, OR (US); Dawn Gayle Flakne, Portland, OR (US); Alan Fryer, Portland, OR (US); James Lowry, Tualatin, OR (US); Rainer Joerg Grosskopf, Portland, OR (US)

(73) Assignee: BIOTRONIK SE & CO. KG, Berlin (DE)

( * ) Notice: Subject to any disclaimer, the term of this patent is extended or adjusted under 35 U.S.C. 154(b) by 0 days.

(21) Appl. No.: 17/747,129

(22) Filed: May 18, 2022

(65) Prior Publication Data

US 2022/0392630 A1     Dec. 8, 2022

Related U.S. Application Data

(60) Provisional application No. 63/196,875, filed on Jun. 4, 2021.

(30) Foreign Application Priority Data

Jul. 1, 2021 (EP) ..................................... 21183208

(51) Int. Cl.
*G16H 40/67* (2018.01)
*H04L 67/10* (2022.01)
*H04W 4/20* (2018.01)

(52) U.S. Cl.
CPC ............. *G16H 40/67* (2018.01); *H04L 67/10* (2013.01); *H04W 4/20* (2013.01)

(58) Field of Classification Search
CPC .......... H04L 67/10; G16H 40/67; H04W 4/20
See application file for complete search history.

(56) References Cited

U.S. PATENT DOCUMENTS

| | | | |
|---|---|---|---|
| 7,369,897 B2 | 5/2008 | Boveja et al. | |
| 2010/0094098 A1* | 4/2010 | Smith ................ | A61B 5/14551 600/300 |

(Continued)

FOREIGN PATENT DOCUMENTS

WO    WO 2020/083585 A1    4/2020

OTHER PUBLICATIONS

Extended European Search Report dated Jan. 4, 2022, for Application No. 21183208.4, 9 pages.

*Primary Examiner* — Benjamin M Thieu
(74) *Attorney, Agent, or Firm* — Frost Brown Todd LLP

(57) ABSTRACT

A system includes at least one medical device (7), a remote monitoring server (RMS, 1) and at least one patient remote device (PR, 5). The the PR is configured to establish a first bidirectional communication connection (12, 14) of the PR and the RMS and a second bidirectional communication connection (13, 14) of the PR and one chosen medical device, wherein the PR is further configured to manage remote processes associated with the chosen medical device comprising remote interrogation of the chosen medical device and remote programming of the chosen medical device using the second bidirectional communication connection as well as data exchange with the RMS concerning interrogation data and/or program data with regard to the chosen medical device using the first bidirectional communication connection.

15 Claims, 10 Drawing Sheets

(56) References Cited

U.S. PATENT DOCUMENTS

| | | | |
|---|---|---|---|
| 2011/0161111 A1* | 6/2011 | Dicks | A61B 5/0022 |
| | | | 705/3 |
| 2013/0191513 A1* | 7/2013 | Kamen | H04L 67/02 |
| | | | 709/219 |
| 2017/0120062 A1 | 5/2017 | Kumar | |
| 2018/0028827 A1 | 2/2018 | Schilling et al. | |
| 2020/0086128 A1 | 3/2020 | Rondoni et al. | |

* cited by examiner

SYSTEM AND METHOD FOR DATA INTERROGATION AND/OR REMOTE PROGRAMMING OF A MEDICAL DEVICE

This invention disclosure describes a system and method to provide remote programming of medical devices and/or interrogation of data from medical devices.

Medical devices such as implants as known in the art can be coupled with various external devices to exchange data. For example, an implantable medical device can be coupled with a programmer that allows a health care professional (HCP), such as a clinician, to adjust the is implantable medical device's settings. For coupling, a magnetic switch can, for example, be used which is placed over the implantable medical device. The magnetic switch has a permanent magnet whose magnetic field is detected by the implantable medical device and puts it into a coupling state in which the implantable medical device is coupled to the programmer.

In addition, in a wireless monitoring system, a patient device is known to connect wirelessly to a medical device when located near the medical device. Such patient devices are used, for example, to download patient data at regular intervals (e.g., daily) from the implantable medical device and forward it to a service centre. At the service centre, the data are pre-processed and, if necessary, transferred to a user, e.g., an HCP.

A patient device may, for example, be equipped with a wake-up function to switch an associated implantable medical device from a resting state to an active state in order to establish a communication link with the implantable medical device. The patient device for example emits a wake-up signal in a radio frequency (RF) range, which is received by the implantable medical device, whereupon it is activated for data communication with the patient device.

A potential disadvantage of a general wake-up functionality to wake up an implantable medical device is that unwanted access to the implantable medical device can potentially be gained by third-party devices that implement the patient device's communication scheme and methodology. Especially, in the field of implantable medical devices with vital therapy functions such as pacemakers and implantable cardioverter defibrillators, demands on cybersecurity are generally high.

In addition, systems exist providing the possibility for a patient to initiate a recording of data by the implantable medical device. If, for example, a pacemaker patient does not feel well, e.g., if the patient feels dizzy or experiences a tachycardia, the patient can trigger the recording of an ECG by the implantable medical device, e.g., by actuating a remote control. The data recorded in this way is transferred directly to an HCP or to a service centre the next time data is retrieved from the implantable medical device, for example during an examination at the clinician or via an automatic query of the patient device.

Generally, processes to access real-time status data from an implantable medical device, such as an implantable pulse generator (IPG), are presently limited to interrogated data gathered during an in-clinic follow-up or, in limited examples, a report triggered by the patient. These processes lack clinician control. Although some implantable medical devices have means for triggering an interrogation when the patient is remote from a clinician, the patient generally is involved as actor able to trigger the remote interrogation, the clinician currently having limited ability to trigger the remote interrogation by himself.

In a typical workflow, as provided by some products currently available, a patient, who feels symptomatic, may wish to send a report to a clinic, or the clinic may request that the patient generate a report. In either case, the patient follows the process to initiate the patient device to trigger the interrogation. This requires either that the patient places an interrogation wand over the implanted medical device, or if available, the patient device can connect to the implanted medical device via wireless means. The implanted medical device processes the interrogation and transmits data to the patient device. The patient then triggers the patient device to transmit an interrogation message, for example, to a service centre, or if available, the patient device initiates the transmission to the service centre automatically.

Thus, such solutions are patient-triggered in the sense that clinicians must rely on the patient to initiate the data capture and possibly the data transmission as well, and are therefore not in control of how or when the data is captured. Further, as the clinic cannot control receipt of the information transmitted from the implant, an HCP is not necessarily able to respond to the receipt of the data at the time it is received. This leads to a non-optimal workflow regarding the clinic review of the data. Because the transmission of data triggered by the patient and the receipt and review by the clinic are disconnected from one another, potentially a liability situation may be caused, if the clinic does not respond in a timely fashion.

U.S. Pat. No. 7,369,897 discloses a method and system of remotely controlling an implanted stimulator for providing electrical pulses to nerve tissue, comprising an implantable stimulator, an interface unit, and a mobile device such as a modified PDA or cell phone. Document WO 2020/083585 A1 discloses a method for initiating a data transfer from an is implantable medical device. This document provides a means to remotely interrogate an implantable medical device via a trigger initiated by a clinician. Having the process triggered by the clinician rather than the patient allows the clinician to be in control of the process.

State-of-the-art implanted pacemakers, cardiac monitors, neuro stimulators and similar implantable medical devices communicate with an HCP user interface during a face-to-face visit with an HCP. During the face-to-face visit the programmer provides a real-time view of diagnostic and technical data.

SUMMARY

Typically, these implanted devices can also transmit diagnostic and technical data periodically to a server. HCPs access this data through a secure website. This enables them to remotely track their patients. However, the data transmission delays in existing remote monitoring designs are too limiting for HCPs to provide more complex care to their patients. For example, neuro stimulation systems require interactive feedback from patient to clinician in order to adjust the stimulation therapy effectively. Providing such interactions remotely is not possible with today's systems. In cardiac rhythm management, it is desirable for the clinician to be able to view an IEGM and device status in real-time if the patient is suspicious of an event. Further, a clinician-triggered programming or interrogation of the medical device is desired, wherein a safe communication is required.

Accordingly, there is a need to provide safe data interrogation or device programming remotely and in real-time based on patient interaction.

The above object is solved by a system having the features of claim 1 and a method with the features defined in claim 12, by a computer program product having the features of claim 14 and a computer readable data carrier according to claim 15.

Particularly, the above object is solved by a system comprising at least one medical device, a remote monitoring server (RMS) and at least one patient remote device (PR), wherein the PR is configured to establish a first bidirectional communication connection of the PR and the RMS and a second bidirectional communication connection of the PR and one chosen medical device, wherein the PR is further configured to autonomously or user-driven manage remote processes associated with the chosen medical device comprising remote interrogation of the chosen medical device and remote programming of the chosen medical device using the second bidirectional communication connection as well as data exchange with the RMS concerning interrogation data and/or program data with regard to the chosen medical device using the first bidirectional communication connection. The user may be the patient, the HCP or a technician.

In one embodiment, the management of remote processes in the at least one PR comprises a validity check on a program for remote programming of the medical device (i.e., the required number of electrodes/anodes/cathodes must be defined for a program to be valid.).

In one embodiment, the at least one PR is configured to support video and/or audio call functionality simultaneously with displaying interrogation data of the medical device and/or to provide patient surveys, patient information push to the HCP and/or patient appointment requests. This requires that the PR provides an error-proof connection with no technical steps required by patient. This has the advantage that it brings flexibility for smartphone/web-video on the PR.

The above system has the advantage that the PR serves as an autonomous or user-triggered control node between the RMS and the medical device for remote programming and interrogation of data and may thereby also realize a safe communication as indicated below in detail. The functionality provided by the PR may be realized by corresponding hard- and software, wherein in one embodiment the standard hardware of the PR is used. In the latter case, corresponding software only, e.g., an app, is provided and installed at the PR which realizes the above and below described functionality. In one embodiment the app comprises a user interface (UI) for the patient and/or the HCP.

In one embodiment the system further comprises at least one HCP remote device (CP), i.e., a remote device for an HCP, wherein the at least one CP is configured to establish a third bidirectional communication connection of the at least one CP and the RMS in order to provide additional real-time remote programming and/or interrogation of the chosen medical device using the at least one CP via the RMS and one PR corresponding to the chosen medical device. In case no CP is used for remote programming and/or interrogation of the chosen medical device this may be triggered by the RMS, for example at pre-defined, regular intervals.

The whole system may be managed, operated, established and/or sold by a system provider which may provide the hard- and/or software of the system to the user (HCP, patient, technician). The technician may belong to the system provider. The system provider may be a commercial enterprise and/or health facility.

In one embodiment, the system is configured to maintain the first, second and/or third communication connections as continuous communication connections.

The above system has the advantage that communication is provided in real time, via individual system devices automatically interacting in order to facilitate a continuous data stream. The system described further provides HCPs continuously with up-to-date information about their patients while the patients are going about their daily lives. This information may be retrieved by the HCP from the RMS on demand. The reduced latency and increased availability of longitudinal data (i.e., data that tracks the same sample at different points in time) provided is expected to result in improved quality of care for the patients and efficiency in the clinic workflow.

The system provides real-time, remotely triggered data update from and remote communication to the medical device, using either the CP or the PR. The system comprises an integrated network of the at least one medical device, for example an implanted medical device (IMD), the at least one patient remote device (PR), e.g. a device comprising a transceiver and/or a therapy control device, with a patient user interface (UI), the RMS forming a service centre comprising a central processing (and optionally admin) unit, and the at least one CP as an HCP device (e.g. a computer, a tablet or a notebook, also called programmer) with a HCP user interface (CUI) for remotely programming the medical device. The mentioned system components may communicate via public or private communication networks. Remote programming according to the invention realizes the use of a CP with a live connection to the RMS and the PR and the medical device.

The system may be used for triggering a real-time interrogation of the patient's medical device current data, for remote analysis of current and historical patient data, and for remote communication to the medical device, all done during a continuous session between the HCP user interface (CUI) and the medical device or during a continuous session between the PR and the medical device, the PR having a continuous session with the RMS. According to the invention, this system may also be used for remote programming of the medical device. Additionally, the continuous or intermittent communication to and programming of the medical device is also provided by the PR.

The invention may be used in multiple areas of medical device application, e.g., spinal cord stimulation (SCS), cardiac rhythm management (CRM), and many other medical fields that utilize an implanted medical device e.g. deep brain stimulation (DBS), occipital nerve stimulation (ONS), trigeminal nerve stimulation (TNS), vagal nerve stimulation (VNS), phrenic nerve stimulation, gastric electrical stimulation, and sacral nerve stimulation (SNS). The inventive system manages the elements of the system to reduce impact to the medical device battery longevity of the remote connectivity process.

In one embodiment, the at least one PR is a computer, tablet or a smartphone. In particular, the PR may be an off-the-shelf smartphone, e.g., Android smartphone. In one embodiment the at least one PR, e.g., if it is a smartphone, is configured to restrict and/or to prohibit pre-defined built-in functionality of the at least one PR, e.g., control panel options, the phone App, SMS messenger, Internet browsing, and the Google Play Store. Use of an off-the-shelf smartphone reduces the technical variables in the system, which is a benefit for an initial product market introduction. The PR, e.g., the smartphone may be provided by the vendor of the system. In one embodiment, the PR is a smartphone in the form of a "Bring Your Own Device" (BYOD) mobile device, e.g., with another one than Android OS, which is not provided by the vendor of the system but the user. In fact, the app is designed with the idea of running on patient owned devices. This is, in particular, realized by the use of SOUP libraries designed for this purpose. In one embodiment specifically Xamarin technologies are used provided by Microsoft® designed to enable applications that can run on a variety of platforms. In one embodiment, the smartphone used as PR is used with no hardware modifications, with an OTS operating system and an OTS Mobile Device Management (MDM) system. The PR is configured to support other tool functionality like patient surveys, patient information push, patient appointment requests, all done within the secure medical device environment provided by the above-defined system.

In one embodiment, an MDM is software providing administration and monitoring of mobile devices used as PR, such as smartphones, tablet computers, laptops and desktop computers. MDM allows administration of mobile devices across a business enterprise. In this invention, the MDM provides a solution for the external programmers (EP) (e.g., the CP and PR) of the system that offers controlled software environment for medical device, control of OS of the EP, control of apps included in the EP, fleet management of the deployed EPs (see below) and security, e.g., ability to do a remote wipe of the EP under control, which means that the data stored in the respective EP are removed. Further, in one embodiment the at least one PR provides a user interface platform configured to intervene and/or control the management of remote processes in the at least one PR by the patient and/or HCP.

With regard to the embodiment in which a smartphone is used as a PR, the smartphone is connected to exactly one MDM. In this embodiment the MDM has access to all the phone data and functions in the registered smartphone. It limits access to phone functions and mans ages all aspects of the app. This embodiment further provides for in-house enrollment/processing of devices; no user involvement is required. In this invention the MDM is used for PR s/w version and settings control, i.e., the device is configured initially before the patient receives it, and maintained under control throughout patient's use, by the MDM system.

In one embodiment, the at least one PR is configured to monitor and control incoming and outgoing communication data with regard to the second bidirectional communication connection. This means that the PR provides a cyber-secure "firewall" between a medical therapy device and its external connectivity system(s), allowing processes typically done only in-office to be done effectively and safely in a remote setting, where the patient has no other means to communicate with clinical staff than via a smartphone (i.e., on-demand device interrogation, on-demand device reprogramming).

In one embodiment, the PR is able to securely receive remote software updates from a service center of the system provider via a local wireless network, a cell phone network and/or Wi-Fi (communication via IEEE 802.11 standard). Further, in one embodiment provisioning of the software into the PR hardware is possible to do after the hardware is manufactured (i.e., it does not require access to platforms internals such as test pins).

The following features may also be implemented in any combination with each other:
  HCP-triggered request for the interrogation of the chosen medical device.
  The HCP-triggered request of the interrogation may be initiated remotely from one or more CUI, e.g. (1+N) CUI where N is a natural number; N=0, 1, 2, . . . .
  The data collected by the interrogation may be viewed remotely at (1+N) UI or CUI (see definition of UI and CUI below).
  Data derived from interrogation are a combination of subjective and objective data.
  Data derived from interrogation are a combination of current and historical data.
  Data presented is collected from (1+N) Data Reporters (N—natural number; N=0, 1, 2, . . . )
  In one embodiment, one or more (e.g., all) steps in the sequence of establishing the first, second or third communication connections may require a "handshake" process that may 1.) ensure cybersecurity and 2.) provide automatic data persistence, communication persistence and communication repetition to ensure that the communication between each component is completed.

As indicated above the inventive system comprises at least the following components:
  At least one individual-patient medical device, for example an IMD or a trial stimulator, also known as "therapy device".
  A Remote Monitoring Server (or RMS), for example a "Neuro Service Center" (NSC) in one embodiment. The RMS is, for example, a hardware and/or cloud-based service centre that facilitates Remote Programming (RP) and data interrogation of the at least one medical device, and may comprise a central repository of data collected by the at least one CP, the at least one PR and/or the at least one medical device, wherein the hardware may comprise at least one computing device or a network of a plurality computing devices, wherein the RMS further comprises the computing functionality described herein; the RMS is a functional unit that performs substantial computations, including numerous arithmetic operations and logic operations without human intervention and may comprise, such as, for example, a desktop computer, a server computer, clusters/warehouse scale computer or embedded system;
  At least one Patient Remote (PR) device that serves as a transceiver to route communication between the medical device and the RMS, and to provide to the patient some aspect of local control of the therapy process. For example, it gives the patient the ability to change the active therapy program of a medical device, for example a medical device for SCS, control its stimulation amplitude, turn stimulation on/off, and view battery status. It may also serve as an external programmer for the medical device.
  In one embodiment, additionally at least one HCP device/programmer (CP) used by HCPs or field technical representatives to program the medical device remotely. The CP may be physical (i.e., dedicated device) or virtual (e.g., via web-based interface to the system, secure connected data reporters).

For communication, public or private communication network(s) (PCN) is (are) used and in each CP an HCP device user interface (CUI), e.g., GUI at the physical CP or web portal at virtual CP and in each medical device a PR user interface (UI). The RMS may further manage at least one PR and at least one CP, which are together called external programmers (EP) in the following.

In one embodiment, provisioning of the above-mentioned devices is done on the "Factory Output Database" (FOD). This creates a special access point to establish trust relationship between the components in the connectivity system and is only available via pathways internal to the system of a specific provider. In the above-mentioned embodiment, in which BYOD is allowed, additional controls will be added to manage those devices put into use from outside the FOD. This will require the use of additional security steps but will remain consistent with normal industry approach i.e., multi-factor authentication as is done for online banking.

For data/signal processing each of the RMS, PR, medical device and, if applicable, CP comprises at least one processing unit which is generally regarded as a functional unit of the respective component, that interprets and executes instructions comprising an instruction control unit and an arithmetic and logic unit. The processing unit may comprise a microprocessor, a controller, a digital signal processor (DSP), an application specific integrated circuit (ASIC), a field-programmable gate array (FPGA), discrete logic circuitry or any combination thereof. Alternatively, or additionally, the processing unit may be realized using integrated dedicated hardware logic circuits, in particular in the case of a medical device due to the small size and extreme power limitation.

Each component may further comprise a data memory which may include any volatile, non-volatile, magnetic, or electrical media, such as a random-access memory (RAM), read-only memory (ROM), non-volatile RAM (NVRAM), electrically-erasable programmable ROM (EEPROM), flash memory, or any other memory device. The data memory may, for example, store buffer data of the respective component as described below.

The medical device may comprise at least one detector detecting at least one bodily parameter of the patient. The detector is connected to the processing unit for processing the determined bodily parameter.

Each component may comprise further units such as a communication unit for communication as indicated in this description and a power supply such as a battery. The communication may be at least partly extracorporeally. The communication may be provided wirelessly. via the patient's body and/or the air using electromagnetic waves, for example Bluetooth, WLAN, ZigBee, NFC, Wibree or WiMAX in the radio frequency region, or IrDA or freespace optical communication (FSO) in the infrared or optical frequency region or by wire (electrical and/or optical communication). The second bidirectional communication connection may be provided such that the PR is associated to a single medical device. Communicating to another medical device requires first to end the present communication connection to a first medical device and then to establish another second bidirectional communication connection to another medical device.

The medical devices, in particular, the implantable medical device's units may be contained within a hermetically sealed housing.

For remote programming (RP) or interrogation, using the PR and the CP, the use of single, serial handshakes between each component of the system is significantly reduced. Each component is designed to autonomously maintain a continuous connection to its respective neighbours, via an on-going session that persists for the duration of the RP or interrogation process, wherein the medical device has a bidirectional communication link to the PR, the PR has a bidirectional communication link to the RMS and the RMS a bidirectional communication link to the CP. For example:

Medical device and PR maintain, for example, a Bluetooth connection while they are in proximity.

PR and RMS maintain, for example a TCP/IP network connection over the internet while mobile networks are available.

CP and RMS maintain, for example a TCP/IP network connection over the internet while mobile networks are available.

RP may require the use of a CP with a live connection to the RMS and a PR corresponding to the chosen medical device with live connections to the RMS and the medical device. The RMS is used as the conduit to:

Route RP commands from the CP to the medical device, via the PR and

Return responses and status updates from the medical device to the CP, via the PR.

The PR may be configured to display status information of the communication connection to the RMS.

In one embodiment, the PR or the CP may trigger data interrogation from a chosen medical device autonomously (e.g., in regular time intervals) or user-driven (e.g., by the HCP or the patient). In one embodiment, when there is an event that changes the status of the PR or medical device, the PR updates. The medical device may have a push mechanism, when there is a status change on the medical device, e.g., a life-threatening event of the patient, it will push an update to the PR. For example, if the user applies a charger, the medical device pushes status change to PR and PR pushes this status change to NSC. In the CP, the polling interval may be session dependent. The CP may poll frequently during RP, however it only replicates for infrequent events (e.g., session start) during an in-office follow-up.

In one embodiment, the PR may send updates without user interaction, automatically and at pre-defined intervals, of the RMS data set. At the pre-defined interval, the PR will automatically send the newest data of the medical device to RMS which the medical device previously sent to the PR.

In one embodiment, the PR sends updates at patient-configurable intervals of the RMS data set without real-time user interaction. At the programmed interval, the PR will get fresh data from the medical device, if the medical device is within communication range, and will send the data to RMS. This is to handle cases where the patient does not typically carry the PR with them. In this embodiment if, without user interaction, at the time of sending the data the PR has no connectivity to RMS, then when PR connectivity is re-established the PR automatically sends an update of the RMS data set. This is to improve chances of transmission success.

In one embodiment, the PR may enable the patient or another user to initiate an update of a data set to RMS. This is a "manual option". This is to handle cases where the patient didn't have the remote within implant communication range for a while, and for troubleshooting connectivity issues.

Further, feedback loops exist between the components to maintain a closed loop of the communication connection of one component with the component adjacent to it in the communication pathway, to proactively assess the status of the communication process and to automatically and immediately process information when received. Each link between one component to the next transmits new data to the next hop in chain as soon as new data is available, thereby reducing transmission latency to (nearly) zero. Additionally, in case of connectivity loss, any system component sends new buffered data as soon as connectivity to the neighbour is restored. The system, i.e. each of the at least one CP, the RMS and at least one PR comprises a data buffer of sufficient depth to sustain occasional loss of connectivity, and to allow the transmission of large datasets.

Each link releases local data storage as soon as the neighbour has received the data payload.

The process is based upon standard, off-the-shelf communication protocols (e.g., TCP/IP) but the data transmission is controlled by methodologies proprietary to the system provider and specific to the device application. For example, proprietary data transmission control comprises: sending alert notifications to request a data transmission, e.g., from the RMS to the PR; routing data to the right medical device, whereby topology information (connection between PR and medical device) can be used; and choosing appropriate signature and encryption keys for the receiver of a data transmission.

Component's specifications used will be specific and optimized for each medical device application. For example, the medical device may adjust its data sampling rate based upon the communication bandwidth available to it (communication with PR), the PR may buffer its data transmission to adjust for bottlenecks downstream of it, etc. The concept is similar to how a video feed over the internet is buffered. In typical modern video transmission, TCP and HTTP are ubiquitous, and most video is accessed over the Web. A video server built on top of TCP/HTTP uses commodity HTTP servers and requires no special hardware or software pieces. In the described process, the components are specific to the particular task, and communication is done via a secured network. The system is designed such that no user adjustment is required during the communication process. Each component in the system may automatically optimize its behaviour within a proscribed range to match the current communication capability.

This results in a system as indicated above. In one embodiment, at first, the HCP may trigger the communication session at the CP using CUI via a session request that is sent to the RMS. In one embodiment, the start of the session provided by the HCP is triggered by the medical device, PR or the patient. For example, the observation of a pathological situation by the patient, the medical device or the PR may initiate a signal comprising the respective information which is then sent by the respective component to the RMS and the HCP. Based on this information, the HCP may trigger the communication session at the CP as described above. Then, the RMS automatically initiates a session with the PR. Handshake with the PR is completed and communication between the two components persists. Afterwards, the PR automatically initiates a session with the IMD. Handshake with the medical device is completed and communication between the two components persists. The medical device then sends an acknowledgement response to the HCP via the PR-to-RMS-to-CP communication chain. Session is established, with all components now connected in real-time. Now, the remote programming may be provided to the medical device and/or data may be interrogated from the medical device using the established and continuous communication chain. Upon completion of the use case, the session initiator indicates that the session is complete and signals the other components to release their handshakes. Throughout this process, only one handshake is required between adjacent components, each communication channel stays open and steady until a closing message is sent, which closes all connections between the devices.

With each system component passing on the data payload from the device upstream from it as fast as it is received, and refreshing its memory buffer continuously to enable receipt of new data, the information as viewed at the CUI is that of a continuous stream, rather than individual packets of information, and is received with very low latency (i.e., similar to a phone call). Compared to the analogy of "a picture taken and sent via text message "for state-of-the-art IMD systems of sporadically connected sub systems, this invention provides a "video conference" where data is streamed between the medical device and the CP (and thereby via the CUI the HCP) for the duration of the session.

The RMS may be hosted by a service provider, e.g., a company external from a clinic. The RMS may comprise at least one of the following services:
Repository of data collected by EP and medical devices.
Repository of keys and certificates for communication of the elements of the system and the HCP or patient via UI or CUI with the system
Facilitates remote programming by routing data to/from their intended destinations.
Communication with an external push notification service.
PR and, if applicable, CP fleet management (via MDM and processes to manage PRs and, if applicable, CPs).
Medical device instance authentication service.
HCP, technician and patient authentication service; and
Database analytic tools.

The invention includes a Fleet Management service, which consists of tools and processes to manage the PRs and, if applicable, the CPs. In one embodiment VMWare's Workspace 1 or other similar MDM is used to manage the EPs. Workspace 1 is used to limit EP functionality such as:
Preventing access to websites not approved by the system provider.
Placing restrictions on apps that users can access.
Limiting access to the App Store such that only the system provider approved apps are installed/updated.
Jail break protection.
Limiting accessibility to EP configuration.

Fleet management can also be used to provide OS updates to the EP, and to provide the tools to change EP App parameters and settings. EP App parameters and settings are stored in the Couchbase Server.

As indicated above, the RMS may serve as a repository of data collected by EPs and medical devices. The latter may comprise home monitoring (HM), which originates from the medical device and is routed to the RMS via the PR. In one embodiment the HM data may be encrypted by the medical device and may only be decrypted by the RMS. In this embodiment, the PR does not have any key to decrypt the data. The RMS's "certificate and key management system" (CKMS) may be used to decrypt the data.

Further, after the above-mentioned communication connections are established from the CP to the chosen medical device as indicated above, the RMS is used as the conduit to route RP commands from the CP to the medical device and/or return responses and status updates from the medical device to the CP.

A hardware and/or cloud server (e.g., Couchbase® server) may be used to store the data in the RMS. The RMS notifies EPs to pull data from the server via push notifications. RMS sends a push notification request to an external notification service (i.e., Microsoft Azure, Google Firebase Cloud Messaging), which in turn is sent to a specific EP.

A subset of data is copied from the RMS to a data warehouse to support internal business functions such as technical forensics, quality monitoring, and clinical studies.

CKMS may be used to generate and store secrets for every manufactured medical device. Secrets, e.g., encryption keys and authentication credentials, are generated during manufacturing and stored into the medical device. Generated secrets are used to cipher data when:
Remote programming data is sent from the RMS to the medical device.

HM data are sent from the medical device to the RMS. RMS uses an authentication management and access service, e.g. Keycloak, for PR authentication. During provisioning, a PR creates a username and password on the authentication management and access service. Subsequently, PRs submit their credentials to the service for an access token, for example, based on JSON Web Token (JWT). The token is then presented to RMS Sync Gateway to gain access. This follows the OAuth 2.0 authorization code grant model. OAuth is an open standard for access delegation, for example, used as a way for Internet users to grant websites or applications access to their information on other websites but without giving them the passwords.

The RMS may provide CP user management and authentication using a Microsoft Azure Active Directory (AAD) which may be integrated in the RMS or may be realized as an external unit connected with the RMS. In the latter case, the RMS interacts with AAD for HCP and patient management operations.

In one embodiment, CPs may follow the OAuth 2.0 authorization code grant model to gain access to the RMS, where AAD acts as the authorization and token endpoints. Once authenticated, the CP is given an access token, which in turn passes to the RMS Sync Gateway to gain access.

The at least one medical device may send/receive data to/from the RMS, via the PR, such that the PR may not decipher the data. Each medical device has unique keys assigned to it at the time of manufacturing.

EPs may communicate to the outside world via either Wi-Fi or cellular network. This introduces a large attack surface that may impact the EP-to-medical device programmability. However, CPs may be protected by the following:

Malware protection and firewall (e.g., Windows Defender malware and firewall).

CP users are granted user rights and thus not able to install software.

Internet resources are whitelisted to resources that are needed for its functionality (e.g., NSC, Microsoft, MDM provider, etc.)

Access to other internet resources, such as Microsoft Store, is inhibited or limited to privately published apps.

PRs may be protected by the following:

No internet browsers installed.

Messaging and phone apps disabled.

Access to other internet resources, such as Google Play Store, is inhibited or limited to privately published apps.

In one embodiment, Couchbase® may be used as the database engine used to store and share data in the RMS. EPs may use Couchbase Mobile, and the RMS may use Couchbase® Sync Gateway and Couchbase® Server. This setup allows for data replication between the mobile client (EPs) and the RMS.

On the PR information may be stored, e.g., in the Couchbase® instance, pertaining to the medical device, which is associated with such aspects as therapy program settings, battery state of charge (SoC), connection state, etc. This data, in turn, is replicated at the RMS.

In one embodiment, when CPs command a change(s) to a target medical device, i.e., a remote programming, the changes are packaged, placed into the local database instance (e.g., Couchbase® instance), and pushed to the RMS. Once received by the RMS, the package is encrypted then authenticated by CKMS using the target medical device's pre-shared secret keys. Because the medical device's shared secret key is only known by CKMS and the medical device, the PR is not able to decipher the package's contents. The PR receives the remote programming package after it has finished synchronizing with the RMS Server.

In one embodiment data transmission between EP and RMS is encrypted, as well as the BLE link between the EP and the medical device. Further, the BLE link may be provided such that it is not visible from outside the provisioned medical system. Further, the BLE link may be provided such that it is only accessible by the provisioned medical system. For example, a 2-factor authentication is used when the CP user (e.g., the HCP) selects a chosen patient's medical device to remotely program. In one embodiment, the RMS is configured to store and/or manage the authentication and/or encryption keys and/or certificates for the at least one CP, at least one PR, at least one medical device as well as for the at least one user of the system, for example, patient, HCP and/or technician. For that, the RMS may integrally comprise hard- and/or software solutions for that or the RMS may be connected to respective hard- and/or software solutions. For example, Microsoft Azure may be responsible for managing this on the backend, and Microsoft APIs may be responsible for managing user input on the CP side (i.e., login mechanism, communication with Azure, handling of 2-factor input, etc.).

In one embodiment, once the CP user has been authenticated, an authentication service of the system returns one unique signed token, e.g., the above mentioned JWT token, to the CP (referred to as the remote programming session token). The CP provides this token to the RMS during every remote programming transaction during the remote programming session. The one unique token is valid for the duration of the current remote programming session; subsequent remote programming sessions require a new unique token, which means the HCP having to go through the authentication sequence again.

In one embodiment, the at least one PR may not be configured to continuously poll the RMS for changes, as that would result in unnecessary overhead on both the PR and RMS (i.e., data usage from the PR's perspective and request processing from the RMS's perspective). Instead, the RMS may interface with an external push notification system, such as Google's Firebase Cloud Messaging system, to send a notification to the target PR corresponding to the chosen medical device. Conceptually, for example, prior or at the beginning of establishing a communication connection or at the beginning of the remote programming session the target PR receives a push notification from the RMS. This notification serves as a trigger to the PR to poll the RMS server at a faster rate. In one embodiment, the notification does not contain detailed information, such as any identifying or secret data.

In one embodiment, remote programming session begins with the CP user (e.g., the HCP) logging into their CP. Regardless of a session type, all CP users must log in. After logging in, the CP user will be able to select the option to start a remote programming session, which will present them with a list of patients they may remotely program.

From a hierarchal standpoint, patients may be organized by their clinic. CP users may be associated with one or more clinics. Therefore, CP users may only remotely program patients' medical devices for clinics that they are associated with.

In one embodiment, 2-factor authentication is required to be provided when the CP user (e.g., the HCP) selects a patient to remotely program. For example, Microsoft Azure may be responsible for managing this on the backend, and Microsoft APIs may be responsible for managing user input on the CP side (i.e., login mechanism, communication with Azure, handling of 2-factor input, etc.). The CP is responsible for sending a request to the authentication service to gain access to the remote programming resource. Once the user has been authenticated, the authentication service returns a signed token, e.g., a JWT token to the CP (referred to as the remote programming session token). The CP provides this token to the RMS during every remote programming transaction during the remote programming session. The token is valid for the duration of the current remote programming session.

Once the code has been authenticated, the CP may pull the latest copy of the target medical device's data from the RMS, and the user will be able to proceed with a remote programming session.

In one embodiment, PRs may be not configured to continuously poll the RMS for changes, as that would result in unnecessary overhead on both the PR and RMS (i.e., data usage from the PR's perspective and request processing from the RMS's perspective). Instead, the RMS interfaces with an external push notification system, such as Google's Firebase Cloud Messaging system, to send a notification to the target PR. Conceptually, for example, at the beginning of a remote programming session the target PR receives a push notification. This notification serves as a trigger to the PR to poll the RMS Server at a faster rate. The notification does not contain detailed information, such as any identifying or secret data.

The following data may be transmitted during a remote programming session (i.e., "signals"). Please note that these data will differ dependent upon the embodiment. The following data may refer partly to a remote programming process of an SCS system which is described here as a typical embodiment.

a) Medical device data
   Medical device data (serial number, medical device type)
   Therapy data (e.g., therapeutic data (packed parameter values, packed data elements, and interface parameters), lead impedance, offset measurements, therapy program selection, stimulation on/off, enable/disable MRI mode, battery state of charge (SoC), status changes, lead info/configuration ("blob" and interface data), medical device alerts, IMD EC App Status, stimulation usage data (used for statistics)
   Personal data (patient name, physician name, hospital, implantation date of the medical device, indication, lead position, lead type and extension information, implanted system component traceable IDs
   Notes
   Patient Identifier (unique ID, serial number of medical device)
b) Technical data
   Technical data/logs (reset, battery, etc.)
   System-based events
   Battery history log
   MRI mode
   Magnet history
   medical device reset log
   EP application log
   application logs
   Error logs
   Audit logs c) Connectivity device data for communication protocols (the system uses the standard data overhead required for the following communication protocols)
   Bluetooth® Low Energy (BLE) (the medical device radio's transceiver may support BLE 5.0, though the product uses BLE 4.2)
   4G
   Wi-Fi
   TCP/IP The RMS is configured to transmit at least part of these data from the RP while the RMS transfers data with the CP.

In one embodiment, for remote programming of the chosen medical device the CP is configured to produce a single program containing the updates and/or changes of the medical device's parameters and to transmit the single program to the medical device via the RMS and the corresponding PR. This is explained in more detail below. Further, in one embodiment the RMS is configured to encrypt the single program received from the CP, wherein the corresponding PR is configured to transmit the encrypted single program to the chosen medical device. Accordingly, the PR cannot decrypt the single program. Decryption is provided by the medical device as explained in detail below.

In one embodiment, the RMS is configured such that its central data repository comprises data having different security level, wherein one example of data with a lower security level are pseudonymized data. Data with a higher security level are personal or private data such as names, addresses, user ID etc. These data need higher protection and can only be accessed by persons having a higher security level.

In one embodiment, in order to provide data of the RMS for further analysis or for assessment of efficacy of the therapy of the at least one medical device, the RMS is configured to be connected with a data warehouse and/or a clinical data warehouse, wherein the data warehouse and/or the clinical data warehouse are configured to import at least a part of the data stored in the central data repository. The warehouses and their operation are further explained below.

Management of specific error conditions of the system is explained in the more detailed description below.

Further, the above object is solved by the method for programming and/or interrogation of one chosen medical device of a system comprising at least one medical device, a remote monitoring server (RMS) and at least one patient remote device (PR), wherein the PR establishes a first bidirectional communication connection of the PR and the RMS and a second bidirectional communication connection of the PR and one chosen medical device, wherein the PR further autonomously or user-driven manages remote processes associated with the chosen medical device comprising the remote interrogation of the chosen medical device and the remote programming of the chosen medical device using the second bidirectional communication connection as well as data exchange with the RMS concerning interrogation data and/or program data with regard to the chosen medical device using the first bidirectional communication connection.

In one embodiment of the method, the system further comprises at least one HCP remote device (CP), wherein the at least one CP establishes a third bidirectional communication connection of the at least one CP and the RMS in order to provide additional real-time remote programming and/or interrogation of the chosen medical device using the at least one CP via the RMS and one PR corresponding to the chosen medical device.

In one embodiment of the method, the first, second and/or third communication connections are maintained as continuous communication connections.

In one embodiment, the method maintains the continuous communication connections until a "close" signal is sent from the one CP to the chosen medical device via the RMS and the corresponding PR and/or from one PR to the connected medical device and the RMS.

In one embodiment of the method, the at least one PR monitors and controls incoming and outgoing communication data with regard to the second bidirectional communication connection (e.g., by a firewall).

In one embodiment of the method, the at least one PR provides a user interface platform which intervenes and/or controls the management of remote processes in the at least one PR by the patient and/or HCP.

In one embodiment of the method, the management of remote processes in the at least one PR comprises a validity check on a program for remote programming of the medical device.

In one embodiment of the method, the at least one PR restricts and/or to prohibits pre-defined built-in functionality of the at least one PR.

In one embodiment of the method, the RMS comprises a central repository of data collected by the at least one CP, the at least one PR and the at least one medical device.

In one embodiment of the method, the RMS and at least one PR comprise a data buffer for communication, and/or the at least one medical device is configured to adjust its data sampling rate based upon the bandwidth of communication with the PR.

In one embodiment of the method, prior or during establishing a communication connection between the RMS and the corresponding PR, the RMS sends a push notification to the corresponding PR thereby triggering this PR to poll the RMS at a faster rate.

In one embodiment of the method, an authentication service is used which provides signed tokens to the at least one CP, wherein one signed token is valid for one particular remote programming session of the chosen medical device.

In one embodiment of the method, for remote programming of the chosen medical device, the CP produces a single program containing the updates and/or changes of the medical device's parameters and transmits the single program to the medical device via the RMS and the corresponding PR. In one embodiment, the RMS encrypts the single program received from the CP, wherein the corresponding PR transmits the encrypted single program to the chosen medical device.

In one embodiment of the method, the RMS is connected with a data warehouse and/or a clinical data warehouse, wherein the data warehouse and/or the clinical data warehouse import at least a part of the data stored in the central data repository. In one embodiment, the respective data of the RMS and/or the data warehouse and/or the clinical data warehouse are accessible to external users depending on the access rights of the respective user.

In one embodiment of the method, the RMS stores and/or manages the authentication and/or encryption keys and/or certificates for the at least one CP, at least one PR, at least one medical device as well as for the at least one user of the system, for example, patient, HCP and/or technician.

The above embodiments of the operation method have the same advantages as the above system. Embodiments of the system indicated above may be realized in the operation method analogously. It is referred to the above explanation of the system in this regard.

The above method is, for example, realized as a computer program which comprises instructions which, when executed, cause the processing units (processors) of the components of the system to perform the steps of the above-defined embodiments of the method which is a combination of above and below specified computer instructions and data definitions that enable computer hardware to perform computational or control functions or which is a syntactic unit that conforms to the rules of a particular programming language and that is composed of declarations and statements or instructions needed for a above and below specified function, task, or problem solution.

Furthermore, a computer program product is disclosed comprising instructions which, when executed by the respective processing units, cause the processing units to perform the steps of the above defined method. Accordingly, a computer readable data carrier storing such computer program product is disclosed.

The present invention will now be described in further detail with reference to the accompanying schematic drawings, wherein FIG. 1 shows one embodiment of the inventive system and the steps establishing the communication between the components of the system;

In the following, embodiments of the inventive system will be explained in detail. The embodiments are explained with regard to medical devices in the form of spinal cord stimulation (SCS) devices and a remote monitoring server (RMS) in the form of a Neuro Service Center (NRS) and with regard to remote programming which may include data interrogation.

Figure 1:
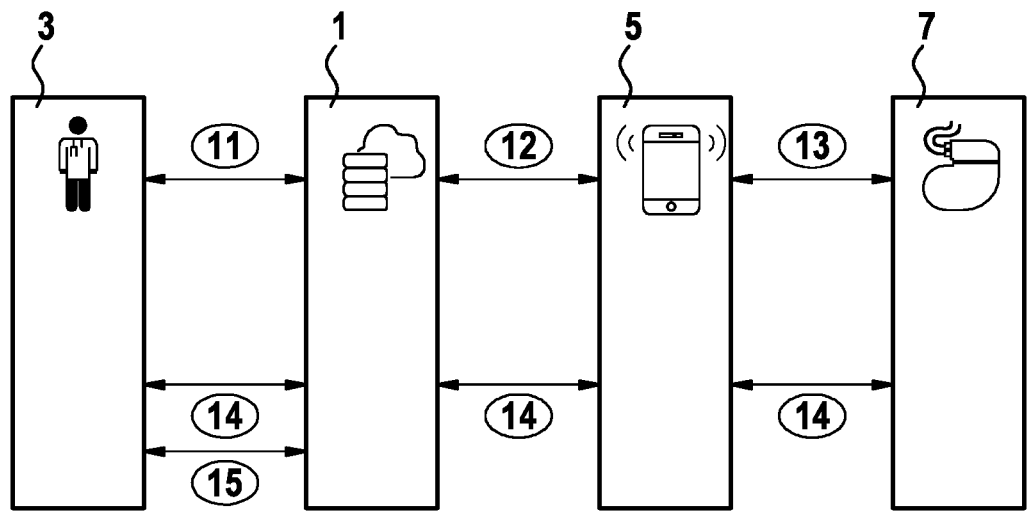

FIG. 1 shows the components of the system, namely the RMS 1, which is, for example, the NRS, at least one patient remote device (PR) 5, and at least one medical device, for example an SCS device, 7. The system may further comprise at least one HCP remote device (CP) 3. For further information with regard to embodiments of these system's components 1, 3, 5, 7 and for their properties it is referred to above explanation in the general description. It is noted that one embodiment of the PR 5 may be an off-the-shelf smartphone having an app realizing the below functionality.

An overview of the remote programming (RP) method may be derived from FIG. 1 comprising the following steps. At first, the HCP triggers the communication session at his/her UI (CUI) at the CP 3 by a session request 11 which is sent to the RMS 1. Then, the RMS initiates a bidirectional communication connection 12 with the PR 5 based on a handshake with the PR 5. In the next step, the PR 5 initiates a communication connection 13 with the medical device 7 based on a handshake process, as well. Then, the medical device 7 sends a response to the CP 3 via the PR 5 to RMS 1 to CP 3 communication chain which is denoted in FIG. 1 with reference number 14. Now a continuous bidirectional communication connection is established between the CP 3 and the medical device 7 with all components now connected in real-time. Upon completion of the use case, the session initiator (HCP) indicates at CP 3 that the session is complete and signals the other components to release their handshakes (step 15). Throughout this process, only one handshake is required between adjacent components, each communication channel stays open and steady until a closing message is sent which closes all connections between the components.

In one embodiment the following protocols may be used:
Medical device 7 to PR 5: Bluetooth Low Energy (BLE)
PR 5 to public communication network(s) (PCN), e.g., 4G LTE, WiFi 802.11
PR 5 to RMS 1: TCP/IP
RMS 1 to public network(s): VPN
RMS 1 to CP 3: TCP/IP Accordingly, the system components of this embodiment and other embodiments may comprise interface modules to communicate via mobile wireless networks (e.g., SMS connection, GPRS data connection, UMTS data connection, LTE data connection), virtual private network(s) or dedicated line(s), internet and local networks via Ethernet or WLAN, electronic patient/case files (electronic medical records) via HL 7 v2 or v3 or similar. Further, suitable communication standards e.g., TLS+TCP/IP, SSL+TCP/IP or ebXML may be used.

Figure 2:
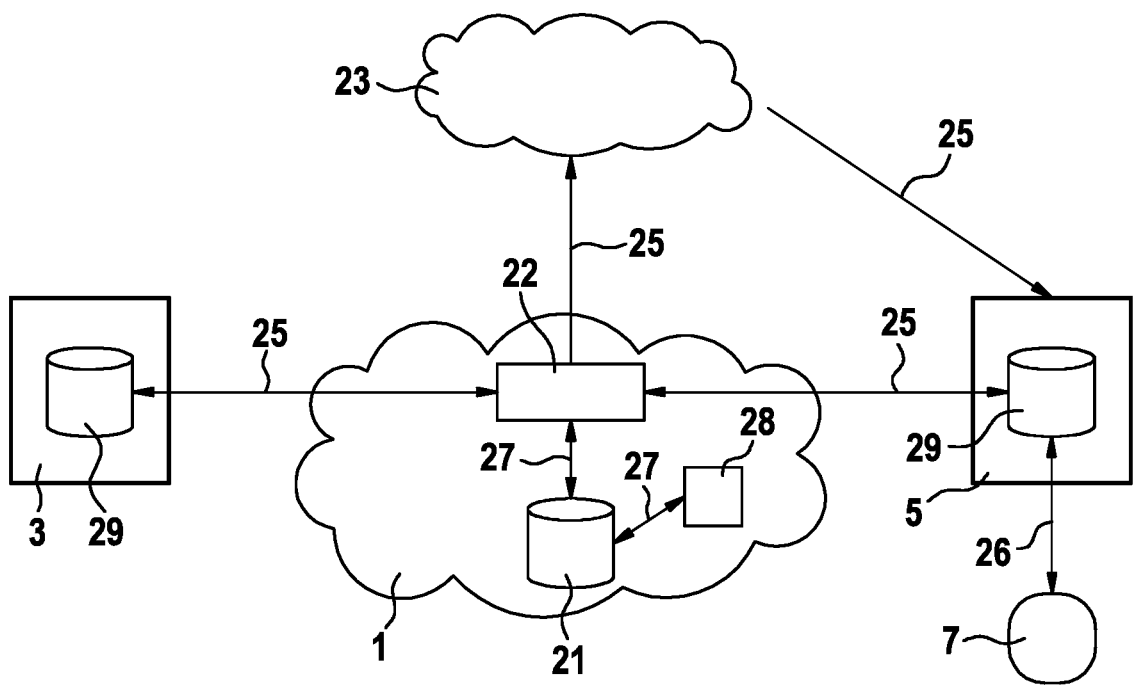
FIG. 2 depicts another sketch of the inventive system.

FIG. 2 contains a different visualization of the whole inventive system. The RMS 1 comprises a Couchbase server 21 as central data repository to store data. Additionally, RMS 1 comprises a Couchbase Sync Gateway 22 for synchronization and communication with CP 3 and PR 5. The system further comprises External Push Notification Services 23 (e.g., Microsoft Azure, Google Firebase Cloud Messaging) in order to notify the CP 3 or the PR 5 to pull data from the RMS 1 via push notifications. For that, the RMS 1 sends a push notification request to the external push notification services 23. In FIG. 2 the arrows 25 represent Internet connections, the arrow 26 a BLE connection and the arrows 27 local network connections (e.g., LAN connections). The RMS 1 further comprises a certificate and key management system (CKMS) 28 which is used to decrypt the data received from the at least one medical device 7. In one embodiment the External Push Notification Services 23 may be integrated in the RMS 1. Further, in order to communicate with the Couchbase server 21 of the RMS 1 the CP 3 and the PR 5 each comprises a Couchbase mobile application 29.

The RMS 1, the CP 3, the PR 5 and the medical device 7 and their bidirectional communication connections are described below in detail with regard to remote programming (RP) initialized by the CP 3. Beside remote programming, the patient may use the PR 5 to control the medical device 7 and to provide remote interrogation of data of the medical device 7 comprising home monitoring routing communication initiated by the patient or automatically triggered. The interrogation data received by the PR 5 may be transmitted at least partly to the RMS 1.

For example, with regard to the SCS system, the patient may determine whether stimulation by the SCS device is turned on or off, may select pre-defined programs stored in the SCS devices or the PR 5, may increase or decrease therapy strength, and/or may change default amplitudes. With regard to remote interrogation, in the SCS system, for example, at least one of the following data are received from the SCS device: battery status/depletion of battery, malfunction of the SCS device, therapy error, therapy parameter.

Figure 3:
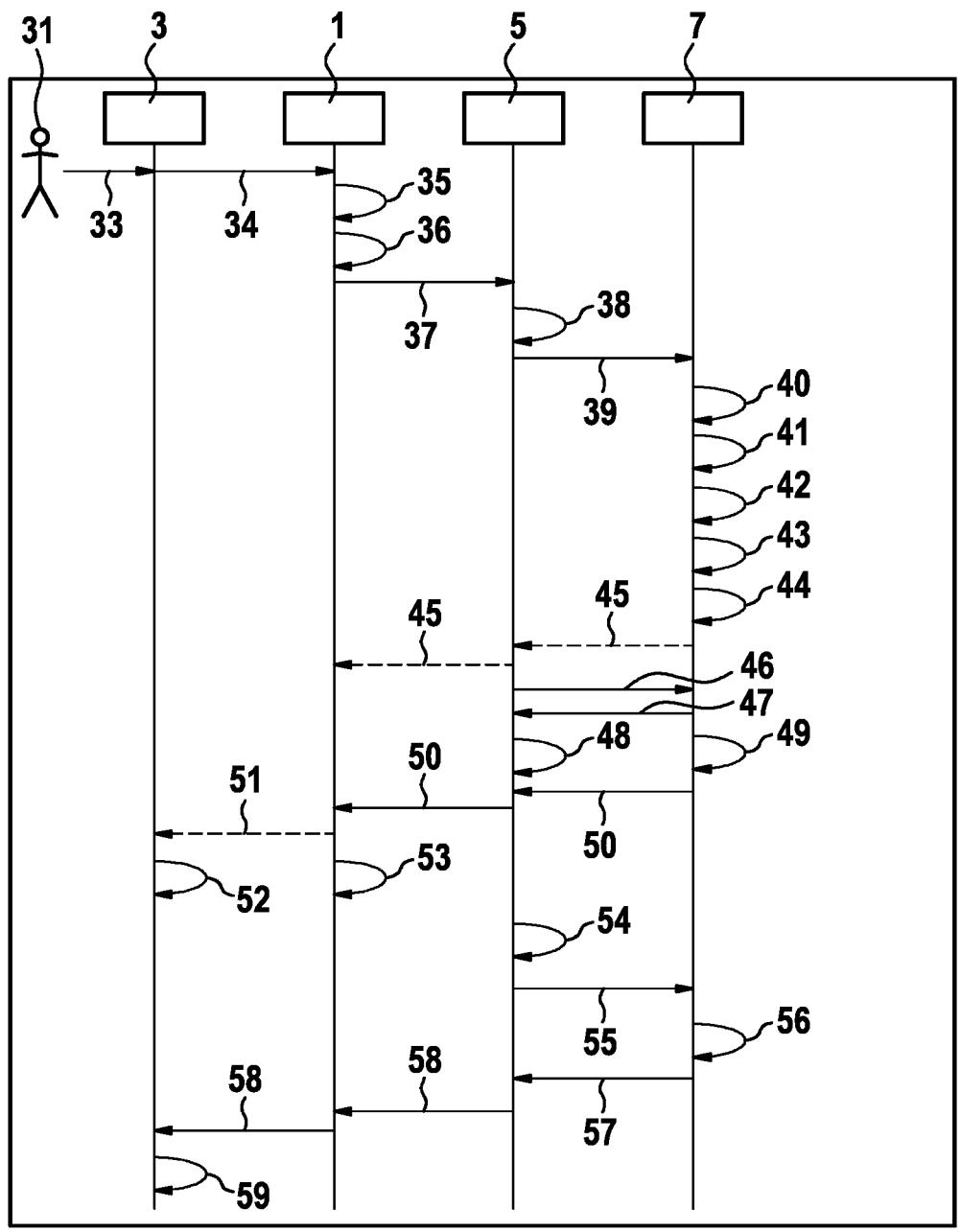
FIG. 3 shows a remote programming overall workflow.

FIG. 3 shows an overall workflow for remote programming which is explained in further detail in the following. The workflow for remote programming works provided the continuous communication connection is previously established between the CP 3 and the medical device 7 after selection of a specific patient/medical device 7 for remote programming. The sequence of events starts with the CP user (e.g., an HCP) commands the transmission of a therapy program using remote programming. As indicated below, the therapy program contains all changes/updates of the parameter of the medical device 7 which are to be programmed. The method describes the process uplink and downlink.

At first, after authentication of the HCP 31 at his/her CP 3 the HCP 31 configures a new therapy program for the patient to be used at its medical device 7. Then, after pressing the transmit button (step 33) the therapy program is transmitted to the RMS 1 (step 34). At the RMS the access token is verified (step 35) and a remote package containing the information of the therapy program is ciphered (step 36). This remote package is then transmitted (automatically, i.e., without further HCP or patient interference) to the PR 5 (step 37). In the next step, the patient is prompted about the fact that there is a therapy program arrived at his/her PR 5 (step 38). In the next step 39 the patient accepts the therapy program and the ciphered remote package is automatically sent to the medical device 7. The remote package is not deciphered at the PR 5 but at the medical device in step 40. In step 41 the therapy program is saved to a buffer of the medical device 7. Step 42 comprises ruling a check to the therapy program in medical device 7 and step 43 and installation and activation of the therapy pros gram. Additionally, in step of 44 the medical device 7 generates and ciphers a remote acknowledgment signal which is to be sent to the RMS 1.

Then, using the continuous communication connection to the RMS 1, the encrypted acknowledgment signal is returned to the RMS 1 via the PR 5 (see steps 45).

Additionally, the PR 5 may then automatically interrogate the medical device 7 for new data. The user driven or automatic interrogation (not within a RP sequence) may be provided analogously. The automatic interrogation during RP is facilitated in step 46, wherein this step contains an interrogation request to the medical device 7. This interrogation request may be sent via the continuous communication connection between the PR 5 and the medical device 7. In response to this request in step 47 the medical device 7 provides the PR 5 with its interrogation data. Then, in step 48 the PR 5 updates its graphical UI. At the same time the medical device 7 generates and ciphers HM PGMR frame in step 49. The PGMR frame contains detailed parameter values programmed in the medical device. In step 50 the PGMR frame is returned to the PR 5 and routed to the RMS 1. The PGMR frame contains detailed parameter values programmed in the medical device. In the next step 51 the latest therapy entities may be pulled to the CP 3. Then, in step 52 the CUI of the CP 3 is updated and at the same time in step 53 the PGMR frame deciphered, data assembled, PPVs unpacked and PDEs as well as appropriate entities at the RMS 1 updated. This allows the system to check the success of the remote programming procedure on the CP and to give feedback to the HCP via the CUI.

In the next step 54 further adjustment of the medical device 7 may be provided by the PR 5, for example, in the case of an SCS a global amplitude may be adjusted. A respective signal, for example, to adjust the medical device's program stimulation amplitudes and to save the global amplitude may be sent to the medical device 7 in step 55. The respective action is provided by the medical device in step 56. In step 57 a response is sent from the medical device 7 to the PR 5 returning stimulation amplitudes. The following steps 58 returns the latest status of the PR 5 to the RMS 1 and the CP 3. Finally, in step 59 the CUI the of the CP 3 is updated accordingly.

In the process described with regards to FIG. 3 the steps 34, 37, 51 and 58 may be Couchbase, commands and responses. Further, the steps 39, 45, 50 may be provided as end-to-end encrypted commands and responses.

Figure 4:
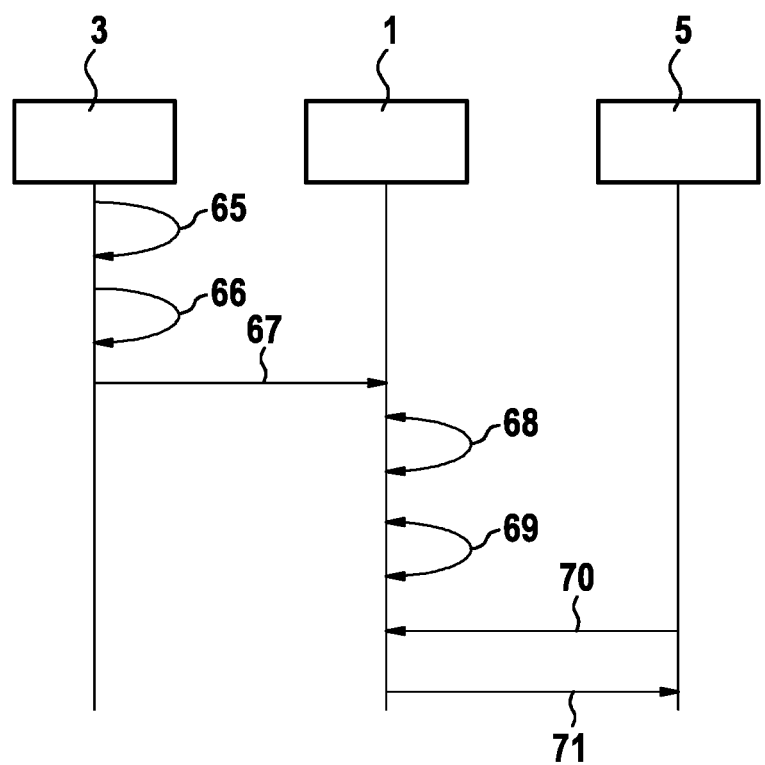
FIG. 4 shows the flow of events for transmission of data to the PR during RP.

FIG. 4 describes the first steps of remote programming using the Couchbase server 21 and Couchbase mobile 29 of the CP 3 in more detail. When CP 3 commands a change to a target medical device 7 (step 65), the changes/updates of the parameters of the medical device 7 are packaged in step 66. Then, they are placed into the local a Couchbase instance by the Couchbase mobile 29 and pushed to the RMS Couchbase sync Gateway 22 and the Couchbase server 21 (step 67). Then, the package or its information is encrypted using the shared keys of the target medical device 7 provided by CKMS 28 (step 68). Because the medical device's shared secret key is only known by CKMS 28 and the medical device 7, the PR 5 is not able to decipher the package's contents. Then, the encrypted remote package is placed into the Couchbase application (step 69). The Couchbase changes are pulled and sent at the next polling interval after it has finished synchronizing with the RMS's Couchbase server 21 (see steps 70 and 71 in FIG. 4).

Figure 5:
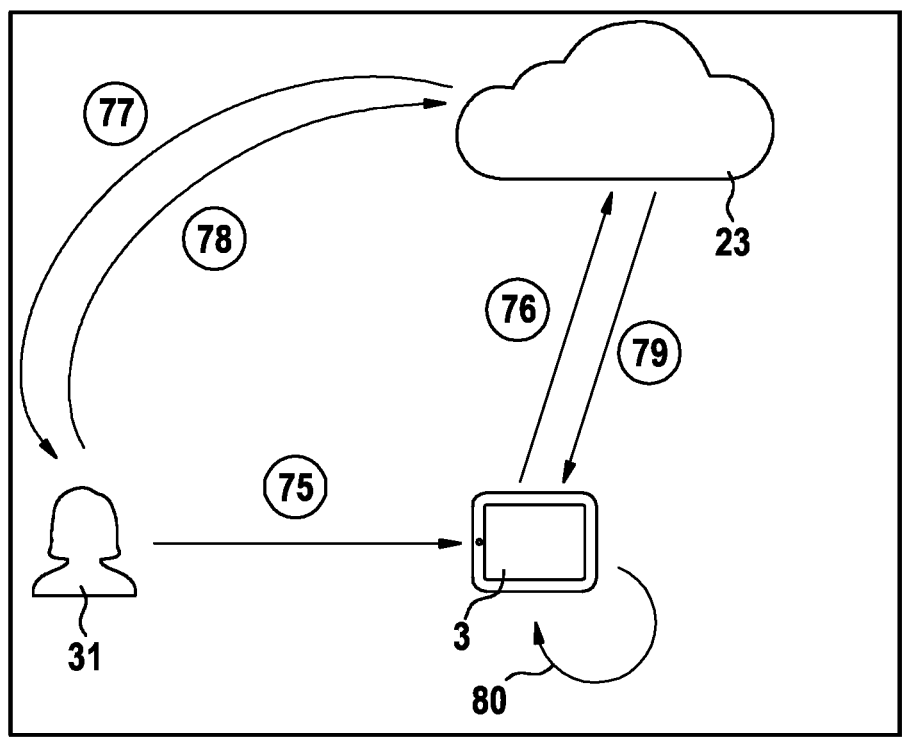
FIG. 5 depicts an example of 2-factor authentication using push notification based approval.

Prior to above programming steps the remote programming process needs to be initiated, which is explained in the following with regard to FIG. 5 showing the start of a remote programming (RP) session after the HCP was logging into his/her CP 3.

Patients may be organized by their clinic. HCP, i.e., CP users, may be associated with one or more clinics. Accordingly, it may be defined that a CP user is allowed to remotely program patients medical devices only for such clinics to which they are associated. In one embodiment, a 2-factor authentication is required to be provided if the HCP selects a patient for remote programming. As indicated above, Microsoft Azure may be responsible for managing this on the back end and Microsoft APIs may be responsible for managing user input on the CP side (login mechanism, communication with Azure, handling of second factor input etc.).

The RP session starts with the HCP requesting to start remote programming in step 75 in FIG. 5. Then, in step 76 user credentials are passed for a remote programming token to the external push notification service 23. In step 77 this service sends an authorization request to the HCP's mobile device and in step 78 the HCP 31 accepts the request. Then the external push notification service 23 returns a signed access token to the CP 3 in step 79. The process then continues with remote programming (step 80).

Figure 6:
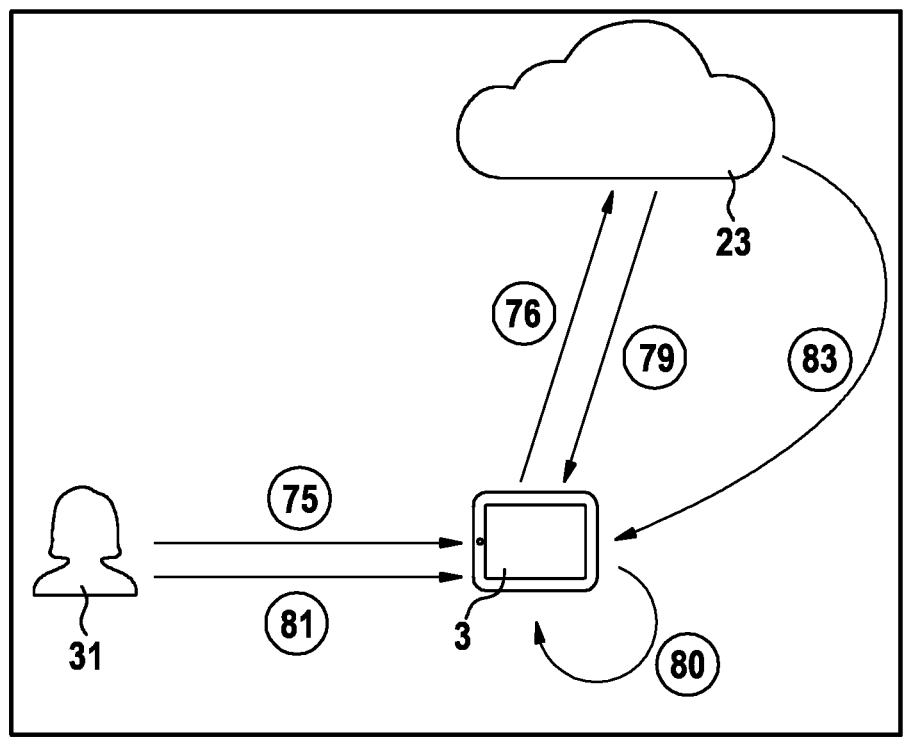
FIG. 6 shows a 2-factor authentication using a 6-digit code (TOTP)

Alternatively, a 2-factor authentication as described with regard to FIG. 5 may be provided using a 6-digit code (TOTP). This is described with regard to FIG. 6. The steps 75 and 76 are identical to the same steps explained with regard to FIG. 5. In the next step 81 the HCP enters a 6-digit code from an authenticator application on his/her mobile device. In step 82 this 6-digit code is passed from CP 3 to the external push notification service 23 via a Microsoft supplied web interface. Then, if this 6-digit code is accepted, in step 83 the external push notification service 23 provides a signed access token to the CP 3 which then proceeds with the remote programming process similar to the method shown in FIG. 5.

The token (MFA token) provided by the external push notification service 23 to the CP 3 is a signed JWT token which is also referred to as the RP session token or access token. The CP 3 provides this token to the RMS 1 in every RP transaction during the RP session. The token is valid for the duration of the current RP session, subsequent RP sessions require a new token which means having to go through the authentication sequence described above again.

In the following steps, the components of the system execute connectivity steps. For that, the following messages/information are utilized by the system and/or the method:

Follow-up ID (a unique identifier for each follow-up session, used for system processing and tracking)

The above-mentioned multifactor authentication token (MFA, i.e., the token of the RP session determined by 2-factor authentication).

RpStartSession message: an entity requesting the start of a remote programming sequence and contains information to specify the target patient. This is used when the HCP selects a patient on the CUI for the remote session. RMS's remote-programming service triggers the associated PR 5 with a push notification as explained above. The PR 5 may start a replication, in case there are a lot of un-replicated data to catch up with.

RpCpRequest message: containing the therapy program parameters

RpPrRequest message: containing encrypted programming commands

RpRmsStatus updates CP 3 with programming progress; captures the status of RMS's processing of the RP request with various timestamps, etc. This message contains, for example, time of RpCpRequest received, time of RpCpRequest signed by CKMS, time of RpPrRequest generated, time of push notification to PR sent, other state and error info.

RpCpStatus. The RpRmsStatus and RpPrStatus entities are used to communicate status at each hop. Each entity may contain tasks that each hop is responsible for performing, errors/status values, completion of tasks denoted by a timestamp.

The remote programming method further makes use of a "Time to Live" calculation (TTL) in its control process. As indicated above, TTL is a value in an Internet Protocol (IP) packet that tells a network router whether or not the packet has been in the network too long and should be discarded. This TTL is an absolute time in UTC. TTL is based on PR's 5 time to account for time synch mismatches between CP 3 and PR 5. TTL is calculated using current PR time acquired at session start and elapsed time since RMS data base synchronization and timeout interval. When PR receives RpPrRequest entity, it takes the TTL value and starts a timer.

Expiration of TTL is communicated by setting the respective value in the RpPrStatus entity.

Figure 7:
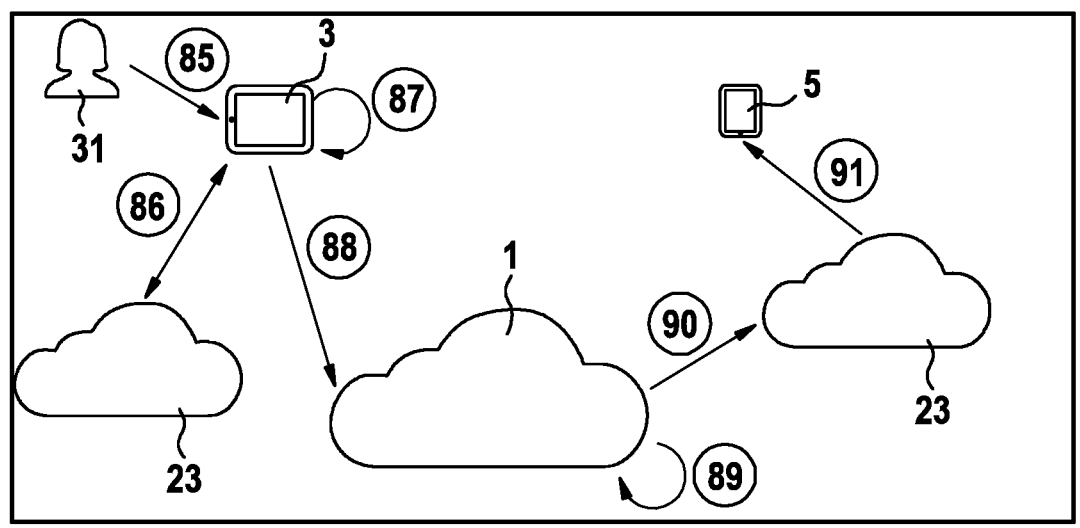
FIG. 7 depicts a flow diagram of initiating an RP session (CP to PR)

With regard to FIG. 7 further steps during initiation of an RP session are explained. This flow diagram shows that the PRs 5 are not configured to continuously poll the RMS 1 for changes as that would result in unnecessary overhead on both the PR 5 and the RMS 1. Instead, the RMS interfaces with the external push notification service 23 to send a notification to the target PR 5. For example, at the beginning of a remote programming session the target PR 5 receives a push notification. This notification serves as a trigger to the PR 5 to poll the RMS 1 (i.e., its Couchbase server 21) at a faster rate. The notification does not contain detailed information such as any identifying or secret data.

For example, the following steps may be executed for remote programming (i.e., remote follow-up). At first, the HCP selects a patient to program in step 85. The HCP navigates to the remote patient management page on the CUI found on the CP 3 and selects a patient from a filterable list of opted-in patients who the HCP is authorized to follow-up with. Then, the 2-factor authentication is provided as indicated with regard to FIGS. 5 and 6 above (step 86). At the same time, the CP 3 creates an entity requesting the start of an RP session (step 87), i.e., the CP 3 sends a RpStartSession command to the RMS. This means that an uplink is created from the CP 3 to PR 5. The CP 3 then waits for successful authentication, and for the PR 5 to respond with an object of the medical device 7 of the patient via RMS 1. Then, the RpStartSession is synchronized with the RMS 1 (step 88). After that, the RMS 1 identifies the target PR 5 which corresponds to the selected patient (step 89), e.g., using Google firebase. Then, a push notification request is sent to the external push notification service 23 (step 90), which contacts the PR 5 corresponding to the selected patient and the PR 5 receives the push notification and is thereby triggered to replicate with the RMS 1 at a faster rate (step 91).

Figure 9:
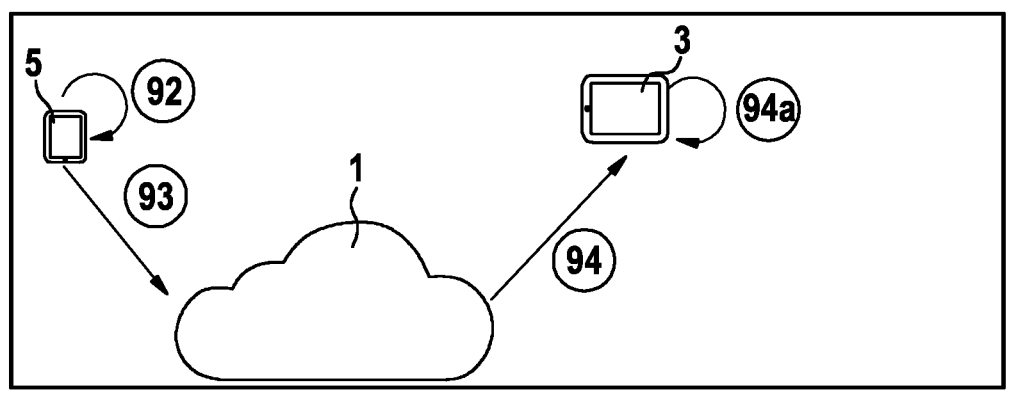
FIG. 9 shows a flow diagram of RP session, namely PR to CP response.

As a response, which is depicted in FIG. 9, the PR 5 synchronizes with the RMS 1 (step 93) after the current PR time and medical device connection state was placed into a response entity (step 92). For example, the current battery state, therapy data such as stimulation state, and/or MRI mode state, and any medical device errors or other data of the PR database will be sent from the PR 5 to the RMS 1. Similarly, the CP 3 synchronizes with the RMS 1 (step 94), wherein the above-mentioned data are further transmitted to the CP 3. Additionally, the CP 3 quotes data from relevant entities to start the remote programming session (step 94 a). Updates to this information will be delivered on a change in any of these items. If the CP user (e.g., HCP) has not begun editing a program, the PR will also update the CP via RMS 1 with any changes to the active program, program strength, or program start strength. Relevant status information will be logged using the normal logging mechanisms. If the response of the PR 5 is received within a pre-defined time (e.g., 30 seconds) of the CP 3 sending the RpStartSession command, and the response indicates that PR is connected to the medical device and has the expected follow-up ID, the CP enters the standard programming page in remote programming mode. Otherwise, CP displays an appropriate message and stays in the remote patient management page.

Figure 8:
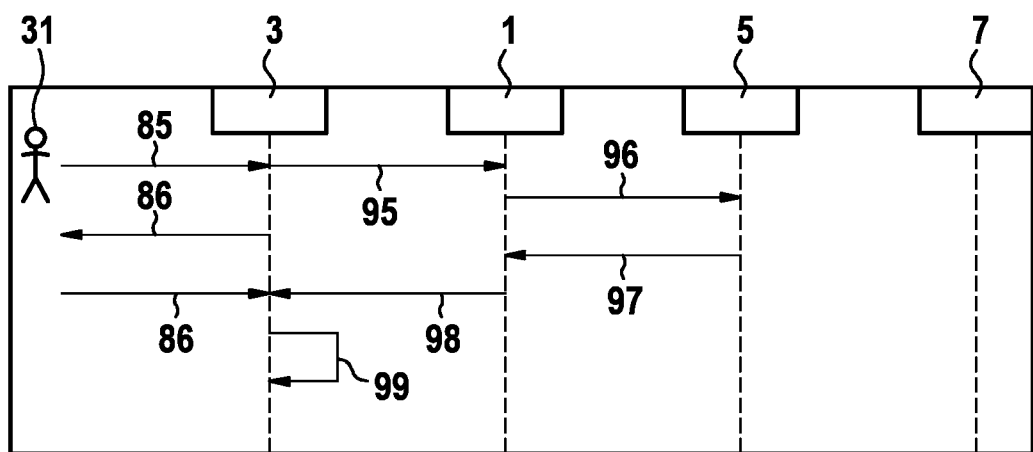
FIG. 8 shows a sequence diagram of initiating an RP session (CP to PR)

FIG. 8 shows the start of the remote programming session as a sequence diagram which is explained in the following. As indicated above the HCP 31 first selects a patient who needs to receive a program update of his/her medical device 7 (step 85). The 2-factor identification illustrated above is provided by the steps 86. Then, a start session command sent from the CP 3 to the RMS 1 (step 95). In the next step 96 the RMS 1 sends a start session notification to the PR 5. Triggered by this command the PR 5 responds by sending information received from the medical device 7 previously (step 97). This information, for example, may comprise current battery state, stimulation state, MRI mode state, or any medical device errors. This information is further transmitted to the CP 3 in step 98. Further, CUI is updated in step 99 afterwards.

In the remote programming mode CP application stages parameter changes provided by the HCP 31 to a single therapy program using the programming CUI. Remote programming differs from face-to-face in that instead of transmitting changes immediately pending changes will be highlighted to indicate to the HCP 31 the changes that will be made. Attempting to switch programs prompts the HCP as the CP user to discard his/her changes or stay on the current program. If the HCP has made all desired changes and taps the transmit button a 'transmission in progress' overlay may be displayed to prevent navigation or further program edits. This overlay may persist until programming completes will be HCP chooses to end the session.

Figure 10:
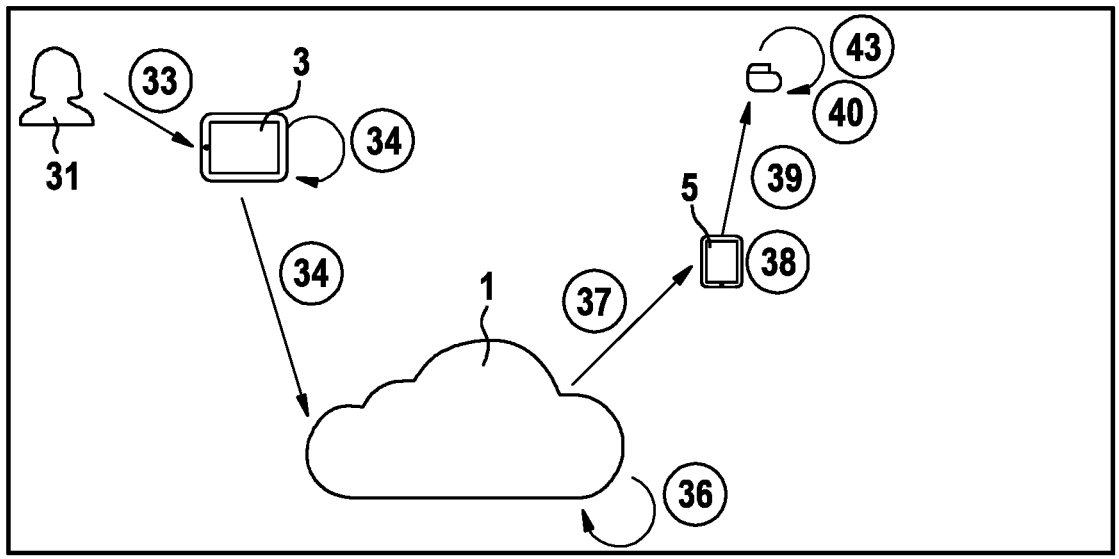
FIG. 10 depicts the RP session communication CP to PR to medical device.
Figure 11:
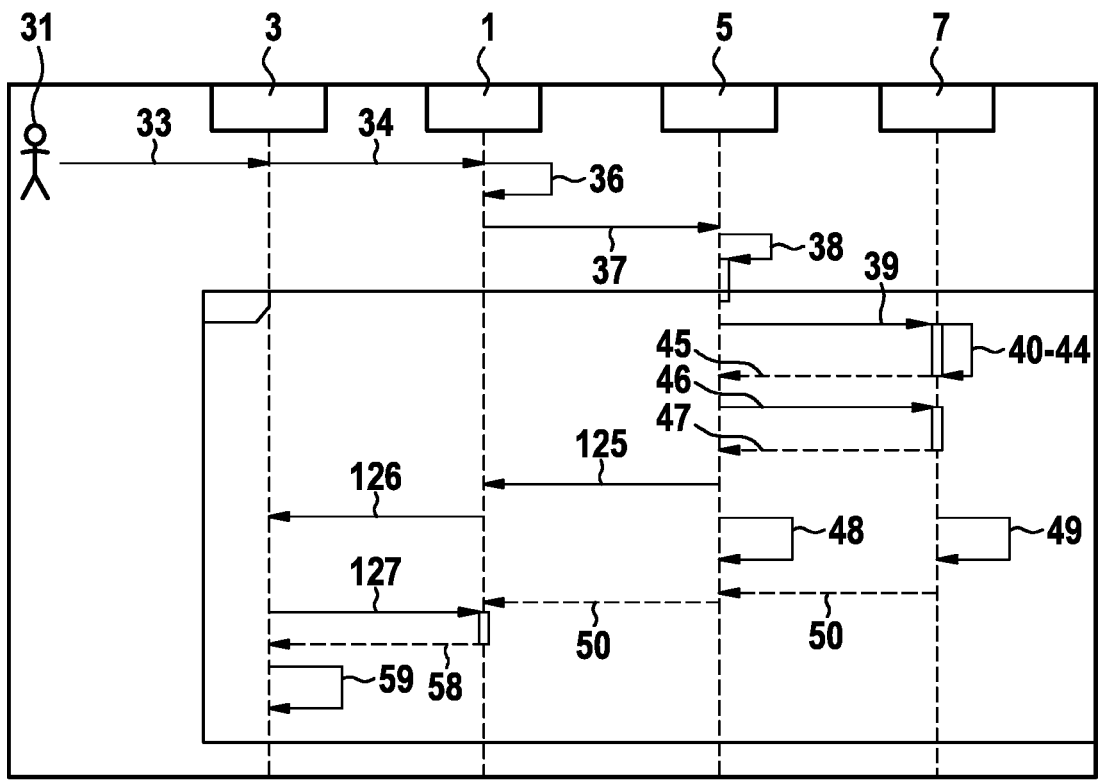
FIG. 11 shows a sequence diagram of RP with transmission acceptance.

The following steps of remote programming are visualized in FIGS. 10 and 11. Pressing the "Transmit" button starts the remote programming using the established communication chain CP-to-RMS-to-PR-to-medical device. The following steps describe uplink and downlink.

For the safety and comfort of the patient, all programs updated through remote programming will have their program strength set to a pre-defined minimum value. After successful programming, the patient may be required to adjust the medical device parameters, for example the strength and default strength to an appropriate level, using the standard PR 3 UI. If the remote programming session is still in progress, these changes will be reflected in the CP 3, as described above.

After pressing the transmit button (step 33, see FIG. 11), to perform the transmission, the CP 3 creates and sends an RpCpRequest entity, containing the therapy program parameters, to the RMS 1 (step 34). After program encryption (step 36), the RMS 1 then sends an RpPrRequest to the PR 5 containing encrypted programming commands (step 37) and creates an RpRmsStatus to update CP 3 with programming progress. The RMS 1 starts a Push Notification to the PR 5 so that the PR 5 may start a replication to get the RpPrRequest update as indicated above. The PR 5 does not parse this data. Upon receiving this request, if the TTL has not expired, the PR 5 asks the patient to accept or decline the program update (step 38).

Figure 12:
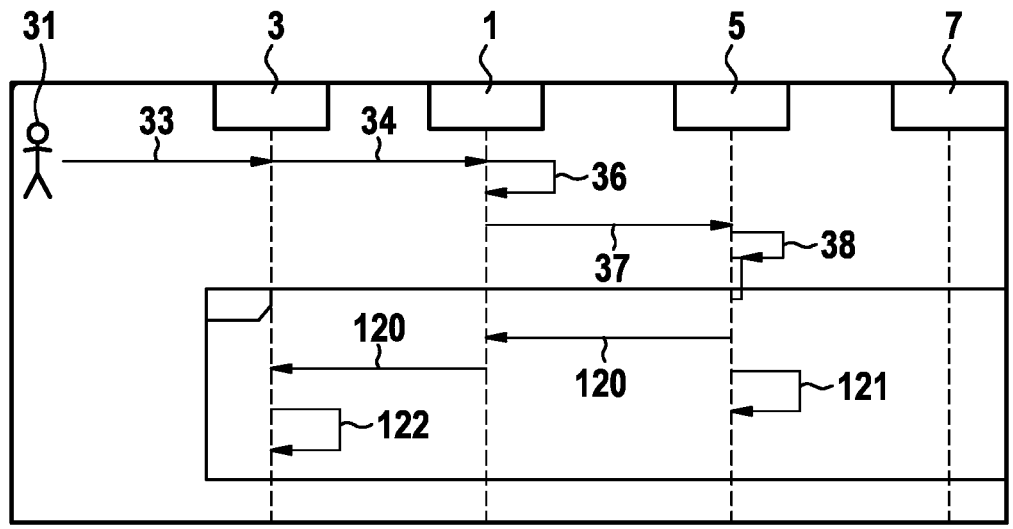
FIG. 12 shows a sequence diagram of RP with transmission rejection.

If the user rejects the update, which is shown in FIG. 12, the PR 3 will insert an RpPrStatus entity indicating the user rejected the update and a message is displayed to the PR 5 and CP 3 users via RMS 1 (steps 120). Accordingly, the UI of PR 3 and the CUI of CP 3 are updated (steps 121 and 122).

If the patient accepts the request in step 38 (see FIG. 11), the PR 3 sends the data to the medical device 7 using, for example, Bluetooth (step 39). The further steps 40 to 44 have already been explained with regards to FIG. 3. Upon completion the PR 5 will resynchronize with the medical device 7 (steps 46 and 47) and sends an RpPrStatus to the RMS 1 to indicate the result of the programming operation (step 125). If the follow-up ID or revision has changed, programming is considered to be successful, otherwise programming is determined to have failed. On successful programming, the CP 3 then receives an updated Follow-up entity from the RMS 1 which is loaded to continue the session (step 126). The following steps 58 and 59 have already been explained in connection with FIG. 3. If programming does not succeed, the CP 3 continues the session as it was prior to the "Transmit" button being pressed. The HCP uses the side menu end session option to end the session once all desired edits have been transmitted.

Figure 13:
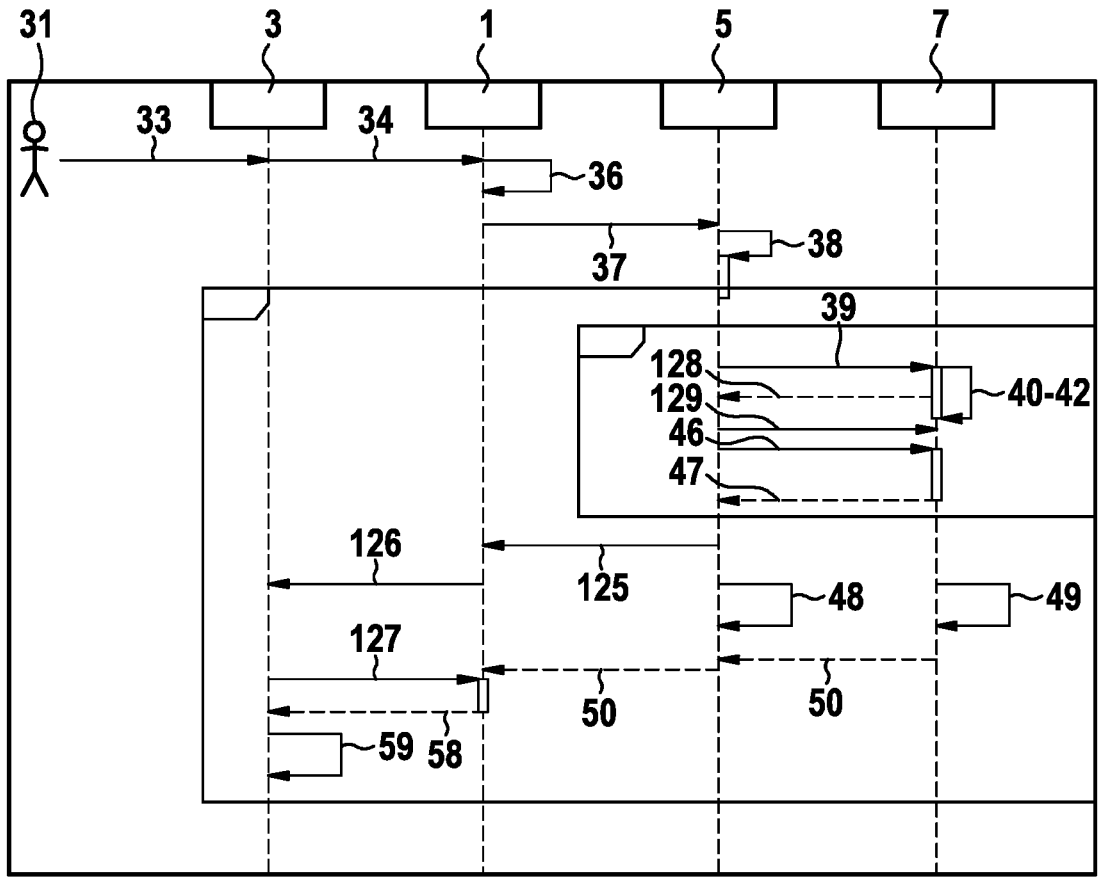
FIG. 13 shows a sequence diagram of RP transmission with connection loss.

During remote programming, it is possible for the PR 3 to lose connection to the medical device 7 which is depicted in FIG. 13 in step 128. In this case the PR will wait until a connection has been re-established (see step 129 in FIG. 13) and then resynchronize with the medical device 7. If after the completed resynchronization the follow-up ID or revision has changed, this will indicate successful programming. If the follow-up ID or revision has not changed the PR will retry the programming operation.

Figure 14:
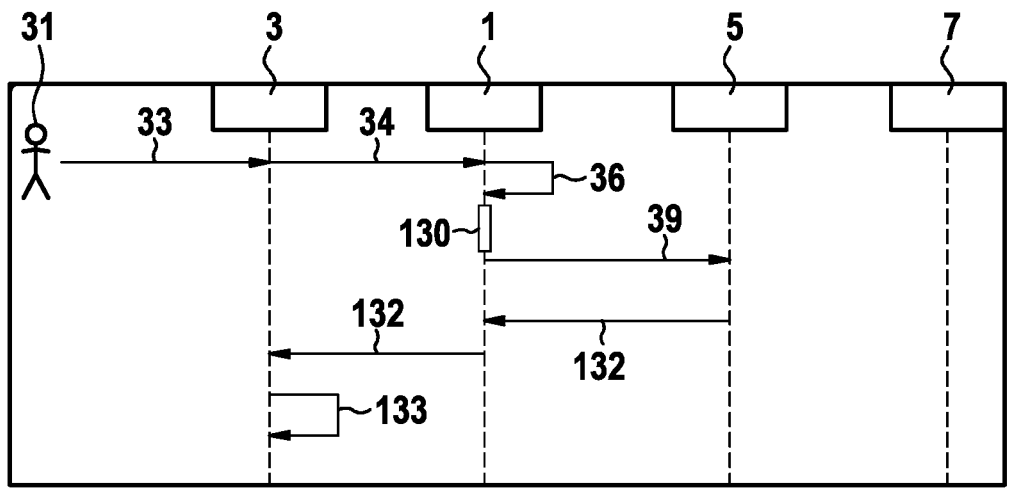
FIG. 14 depicts a sequence diagram of time to live (TTL) expiry before receipt.
Figure 15:
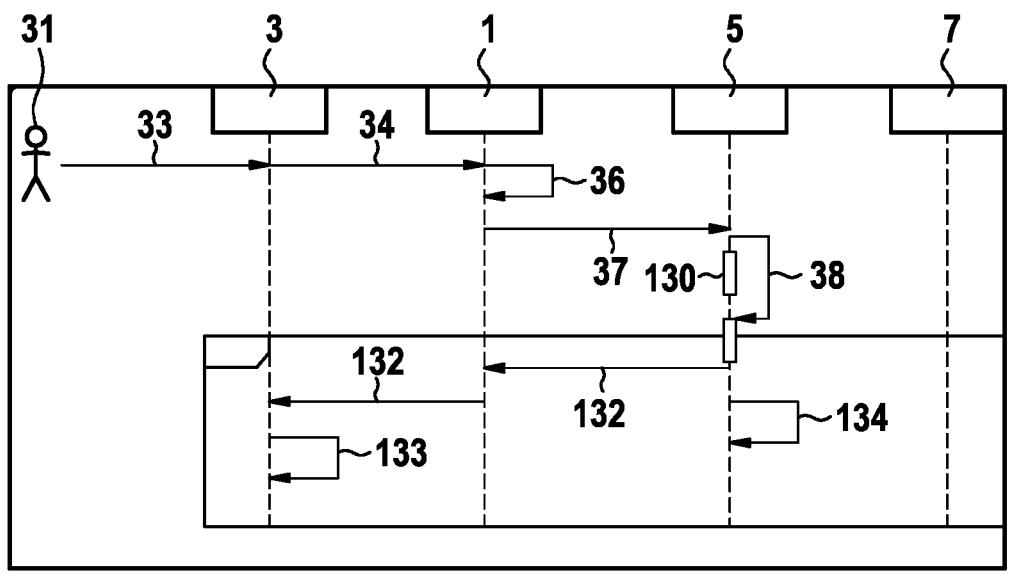
FIG. 15 depicts a sequence diagram of time to live (TTL) expiry before acceptance.
Figure 16:
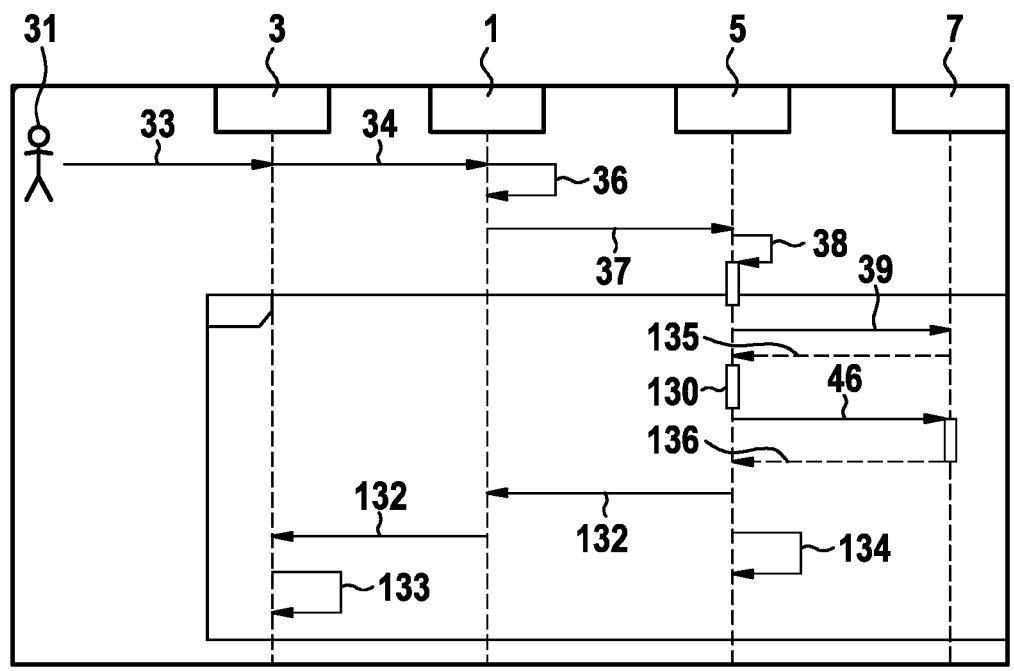
FIG. 16 depicts a sequence diagram of time to live (TTL) expiry during communication loss.

As indicated above, programming transmissions include a Time to Live (or TTL). If the instructions take longer to be transmitted to the medical device 7 than this pre-defined time, which is shown in FIGS. 14 to 16 the programming operation is cancelled. There are three possible TTL scenarios.

In the first scenario shown in FIG. 14, the programming request takes longer to be received by the PR 5 than the TTL. I.e., the TTL expires (see step 130 in FIG. 14) prior the programming request is sent to PR 5 (step 39). In this case, no messages are displayed to the patient at the PR 5 and the PR 5 will send an RpPrStatus indicating the request was cancelled (step 132) which is transmitted via RMS 1 to CP 3, and CP 3 will display an appropriate message to the HCP 31 (CUI update 133).

In the second scenario, shown in FIG. 15, the PR 5 receives the request, but the patient does not accept the request within the TTL (i.e., TTL expiration 130 during prompting of the patient (step 38). This case operates the same as the first case, but an appropriate message is displayed to the patient at the PR 5 (see UI update in step 134 in FIG. 15).

The third case occurs when the PR 5 loses communication (step 135) to the medical device 7 during programming. In this case, which is shown in FIG. 16, once the PR 5 has reconnected with the medical device 7 the PR 5 will check for successful programming using the interrogation step 46. If it turned out that programming has not succeeded (step 136) and the TTL has expired (step 130), the PR 5 will send an RpPrStatus indicating the request was cancelled to CP 3 via RMS 1 (steps 132), and appropriate messages will be displayed to the PR user (patient) and the HCP 31 after CUI and UI update (steps 133, 134).

If, during remote programming, the CP 3 receives a PR 5 or medical device 7 update, or other entity, which indicates the follow-up ID or revision has changed to an unexpected value, the CP 3 will immediately notify the HCP and end the session. This scenario could occur if multiple CP's attempt to conduct remote programming sessions with the same PR 5 at the same time.

Some information needed for remote programming changes very frequently and thus the system does not/may not rely on the standard home monitoring process to transfer this information. For the purposes of PR 5, it needs to be up-to-date at the beginning of the remote programming session but it also needs to be continually updated after the remote programming session so that the CP 3 may see the patient amplitudes change in real time.

The PR therefore performs the following:
1. PR Maintains the PatientDevice entity in its local database which among other things contains:
    a. PatientNonPii DocID (where PatientNonPii refers to patient non-identifiable information)
    b. ApplicationSpecific as a string—This is used for communicating process-relevant information directly between a CP and a PR.
        i. Fuel Gauge Status (i.e. state of battery charge) (displayed on the CP)
        ii. MRI Mode or Not (i.e. enabled or not) (displayed on the CP)
        iii. Status of Master switch (as displayed on the CP)
        iv. Status of Magnet mode (as displayed on the CP)
        v. Current Active Therapy (as displayed on the CP)
        vi. Start Strength and Strength for all programs and sub-programs (merged with data transmitted by HM)
        vii. Connected or not connected state with the implant (displayed on the CP and checked)
        viii. Entity Revision of the follow-up entity from the implant (Checked for compatibility)
        ix. LIM (Lead Impedance Measurement) Enabled (used for calculation rules)
    c. RemoteProgrammingState (i.e.Available, DataOutOfSyncWithImplant, SessionInProgress)
    d. RpStartSessionID—(e.g. null, if no RP session since last PR app launch)
    e. current time on the PR's operating system clock
2. PR Synchronizes this state with the NSC on specific triggers:
    a. At start of RP session
    b. when PR app launches
    c. when BLE connection status changes
    d. when PR associates with a patient & implant
    e. when network connectivity is restored after being offline
    f. when the user taps 'Setting/Advanced/Refresh'
    g. always pushes on when new data is generated
        i. on the reception of a home monitoring message from an implant.
        ii. On any change to a parameter relevant to Remote Programming The system components are specified (e.g., memory, processing capability, transmission speed, etc.) such that they are capable of performing within the boundary requirements of the connectivity use case of the particular embodiment. For example, in the RP embodiment, the components must deliver at least the system throughput requirements for input as set forth below in the following Table:

TABLE

| Inputs | | | |
|---|---|---|---|
| LTE | Download | 22.69 | Mbps |
| (From PR's perspective) | | 2836.25 | KBps |
| PR's speeds based on Speedtest's United States "2017 Mobile Report" (based on Q1-Q2 2017 data) | Upload | 8.51 | Mbps |
| | | 1063.75 | KBps |
| http://www.speedtest.net/reports/united-states/#mobile | | | |
| BLE | Download | 344 | Kbps |
| (From medical device's perspective) | | 43 | KBps |

TABLE-continued

| Inputs | | | |
|---|---|---|---|
| The data rate is based on the assumption of 20 ms Connection Interval CI, the data payload of 215 bytes (MTU size of 251 bytes-36 bytes of App Protocol Overhead), and 4 data packets per CI (in the case of Android). $r = (l\_MTU\ bytes * n\_packets)/t\_CI$ s | Upload | 344 43 | Kbps KBps |
| RP Msg Processing Time | CP | 1 | s |
| | PR | 1 | s |
| | RMS | 15 | s |
| | External Push notification System | 2 | s |
| | TD* | 1 | S |
| medical device BLE Message Processing Latency | | 1 | s |
| RP CMD Payload Size Assuming this is the size of a single program (blob + implant data) | | 3 | KB |
| RP CMD Document Size (Payload + 50% Overhead) | | 4.5 | KB |
| medical device Interrogation Data Size Assuming PR interrogates all 12 programs after it receives an RP Success msg. | | 36 | KB |
| RS RESP Document Size (payload + 50% Overhead) *-Time it takes for TD to decrypt msg (in Mesquite), rule check programm, installprogram, activateprogram, and send alert to PR. | | 54 | KB |
| Hop to Hop Time | | | |
| RP CMD from CP to RMS CP time to encrypt data + time to push data, for example, via Couchbase (ignores Couchbase comm layer activity and takes simple approach of datarate of data size). | | 1.00 | s |
| RP CMD RMS Processing Couchbase (for example) process duration + decrypting data using CP key + encrypting data using medical device key + duration to send a push notification via external service | | 15.00 | s |
| RP CMD from RMS to PR The time it takes for PR to receive push notification + time for PR to pull data from RMS (ignores Couchbase comm layer activity and takes the simple approach of transferring entire data packet based on transmission rate) + PR processing | | 3.00 | s |
| RP CMD from PR to medical device BLE transmission time + medical device processing time (receive msg decrypt msg, run rule check, install program) | | 1.07 | s |
| PR Interrogate After RP Success Resp Assuming PR reinterrogates all programs | | 1.84 | s |
| RP RESP from PR to RMS PR processing time + time to push data to RMS (assuming response sent back to NSC contains latest therapeutic data returned from medical device; ignores, e.g., Couchbase comm layer activity and takes the simple approach of transferring entire data packet based on transmission rate) | | 1.05 | s |
| RP RESP RMS Processing Couchbase (e.g.) process duration + duration to send a push notification via external service. | | 15.00 | s |
| RP RESP from RMS to CP The time it takes for CP to receive push notification + time for CP to pull data from RMS (ignores Couchbase comm layer activity and takes the simple approach of transferring entire data packet based on transmission rate) + CP processing. | | 3.02 | s |
| Total Times | | | |
| RP CMD from CP to PR | | 19.01 | s |
| RP CMD PR to medical device + RP Install in TD (after patient ack) | | 1.07 | s |
| PR Interrogation of medical device + RP RESP PR to RMS + RP RESP RMS to CP (after PR receives RP Success Resp) | | 20.91 | s |
| Round Trip Time (ignoring patient ack time) | | 40.98 | s |

The system further allows combining subjective (e.g., patient diary, patient surveys, HCP notes) and objective data (e.g., current patient status, patient trends and outcomes analysis, longitudinal pain data, activity-based tracking, medication use checking, statistics) into one viewable RMS database via multiple data reporters, for example, CP 3, PR 5, RMS 1 (for example NSC), Electronic Health Record system (EHR). Further, the RMS 1 provides a central service unit that serves as a central data repository of all of clinic's patients, as well as manages access rights and controls access to therapy device data according to user's login. The system may further comprise a web-based presentation layer, accessible from (1+N) different UI. The system may further provide HCP-accessible reporting which includes controlled access to database, configurable access rights within the database (i.e., to specific patient or groups of patients), accessible via multiple portals (CP, NSC UI, EHR UI, other). The HCP may view both current patient status as a real-time "snapshot" as well as via long-term data trends. The reporting may further comprise configurable report formats to allow customization to clinic or individual user's needs. The system further comprises a searchable patient and medical device database.

In the following the data organization/management in the RMS 1 is explained in detail also with regard to data security.

In connection with this, it should be noted all data within the system may be organized such in the RMS 1 that they are accessible to employees of an external service provider (technician of the system provider, external HCP, statistics companies, for example, for patient's studies, companies offering medical devices which may receive further information on the behaviour of their product(s)) via certain tools/interfaces (e.g. a Data Warehouse (DWH), tools for the customer service, etc.), for example, for the purpose of post market surveillance of the used medical devices. The accessible data also include serial numbers, names, dates, etc. Accordingly, access rights are implemented to allow access to exactly that data that each employee needs in order to perform the task at hand. By offering all data via the interfaces of the RMS 1, the necessary access rights and related processes for being compliant with privacy laws may be defined independently of the design, development and maintenance of the RMS.

The concept mainly relies on two principles, namely, to categorize data as close to the origin as possible (i.e., CP, PR, RMS) into different data sets (see "Categories of Stored Data"), and to restrict access to data as close to the data user as possible (e.g., DWH and Customer Service Tools), based on clearance of use.

Medical, technical and connectivity data is collected by stimulators, PRs, CPs and the RMS frontend (the latter only collects data in future generations of the embodiment). Further data might be created during processing.

The data may be accessed by the sub-systems Data Warehouse (DWH) and Clinical Data Warehouse (CDW). If patients have given explicit consents for being included in studies, the DWH may import respective data from the RMS and offer them to service provider's internal users based on the user's access rights. The CDW may import pseudonymized and device identification data from those patients that are part in studies.

RMS may comprise customer support tools for the customer service. These tools may be used for 1st level troubleshooting, customer support and customer administration. There may be an RMS frontend that allows/requires the HCP to directly interact with the RMS 1. In one embodiment external data reporters/consumers will allow for the secure exchange of data between external data reporters/consumers and the RMS.

The data in the RMS, the DWH and the CDW may be stored encrypted. Access rights are in place to ensure restricted access to the stored data. Physical access to the data bases is restricted to administrative staff. The RMS frontend and the RMS customer support tools do not store data themselves but may always request the data live from the RMS 1.

In one embodiment, each access point has a UI designed specifically for the functions performed.

The RMS 1 may also have a user interface which may realize a closed loop, real-time communication with the at least one medical device 7. For example, if the HCP wants to know the patient's data in preparation for follow-up consult or remote assistance call with the patient, the HCP triggers a respective request (update data request) from the RMS 1. This request is then transmitted to the PR 5 which in turn relays the request to the medical device 7. The medical device queries current patient and device status and transmits the report to the RMS 1 via the PR 5. The report is received and processed (i.e., the message is converted to form usable by the RMS 1, scanned for alert conditions using internal algorithms and assigned to the correct clinic and patient) by the RMS 1. Then, the HCP is able to review the new report in advance of the in-person meeting. The interface may be used to display data received via regular routine to connect data automatically (daily, monthly, ... ) or on purpose (e.g., preparation for in-office visit, patient adjustment, ... ). Further, the RMS 1 is configured to provide a current patient status 'snapshot' collected in near real-time showing all quantitative and subjective data store for the patient. In addition, as indicated above, the RMS 1 provides online access to the PR and the medical device to collect real time data. The RMS 1 is further configured to provide the status of the patient's system and statistics collected over time (e.g., for an SCS device implanted lead integrity, present stimulation settings, the diagnostic trends related to pain or system use). In one embodiment, the user may have the ability to configure the display of the combined status such that different data trends are visible or invisible according to the user's preferences. The HCP's web interface of the RMS 1 may further provide an image of the patient, videos or audio files. Further, the interface may allow to query the database, for example for all patients or medical devices under control of the respective clinic.

Additionally, the RMS 1 may provide the feature of an electronic signature ability to allow the HCP and/or patient to electronically provide consent for future participation in remote follow up or scientific studies. Further, the RMS 1 may provide a capability for viewing population wide data for the clinic or for a medical device registry in order to look at overall outcomes or relationships of patient characteristics.

Figure 17:
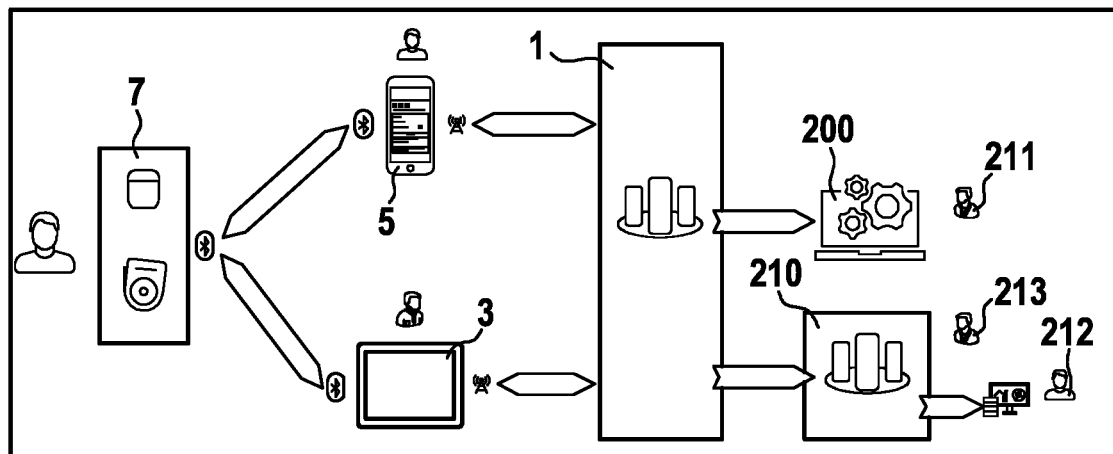
FIG. 17 shows an overview of another embodiment of an inventive system.
Figure 18:
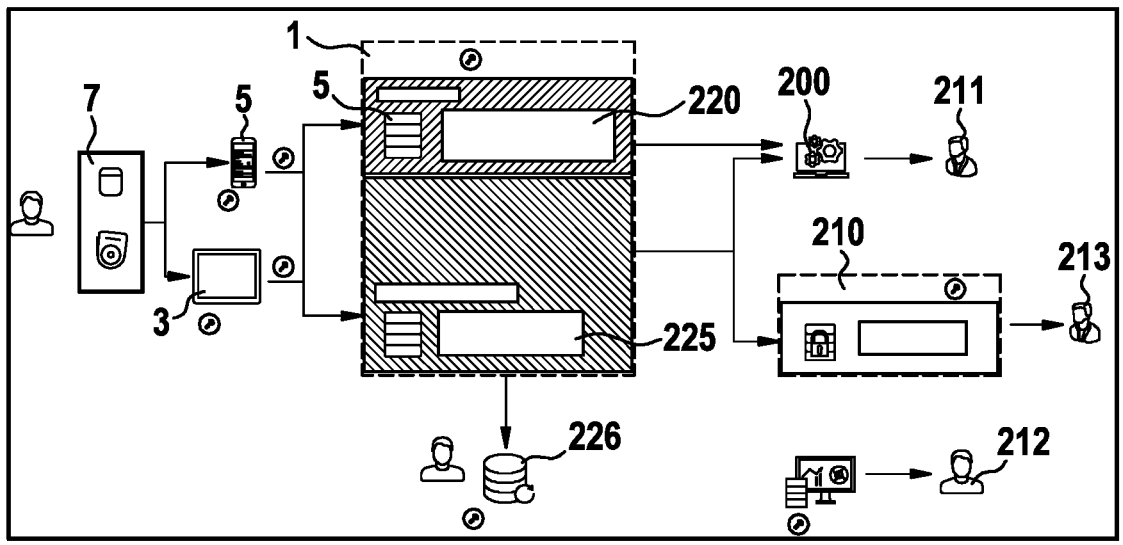
FIG. 18 depicts the embodiment of FIG. 17 in more detail regarding the system architecture.
Figure 19:
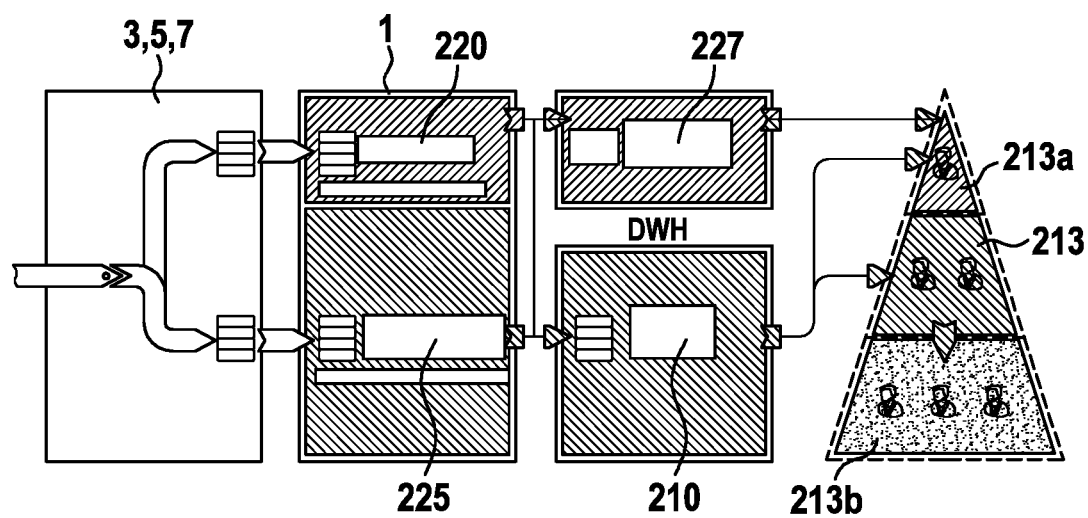
FIG. 19 shows a system data workflow and access diagram of another embodiment of the inventive system.

FIGS. 17 to 19 show different embodiments of data and access organization of the system. FIG. 17 shows that the RMS 1 data are accessible for customer service tools 200 and for a data warehouse (DWH) 210. The customer service tools 200 are used to manage the RMS 1 and to fix problems on the hardware or software side by a technician 211 of the service provider. As indicated above, some of the data available in the RMS 1 may be provided to the DWH 210 for, for example, a post market surveillance or the respectively medical devices. These data may be available for study managers 212 or employees of the medical device manufacturer 213. The systems shown in FIGS. 17 and 18 further provide direct access of the CP 3 to the medical device 7. This may be helpful for in person follow-up the clinic.

FIGS. 18 and 19 show that the data stored in the RMS 1 may be associated with the different security level categories. One part of the data may be private or personal data 220 which need a higher level of protection than the pseudonymized data 225. The private or personal data 220 comprise, for example, names, addresses of patients, HCP or other users, patient record IDs, user IDs. The pseudonymized data 225 may comprise medical data, technical data, serial numbers, patient record IDs, user IDs. As one may derive from FIG. 18 the data warehouse 210 is allowed to access the pseudonymized data 225 only, whereas the customer service tools 200 need to have access to both, personal data 220 and pseudonymized data 225. Further, all data are stored in a backup storage 226.

In FIG. 19 it is shown that the employees of the medical device manufacturer may have different access rights. A first category of employees 213a may have access to personal data 220 via an interim storage 227 and pseudonymized data 225 via the DWH 210. The access to the interim storage 227 is highly restricted. After finishing the tasks using the data of the interim storage 227 these data are deleted. The tasks of this group of employees may comprise contacting users for regulatory reasons or due to discovered issues with specific medical devices or troubleshooting related to personal data 220. The second group and third group of employees 213, 213b have access to pseudonymized data 225, only. The second and second largest group of employees 213 may provide, for example, troubleshooting related to specific medical devices or monitoring of specific medical devices (post market surveillance). The third and largest group of employees 213b provides, for example, statistical monitoring of all medical devices assigned to the system, forward analysis or troubleshooting without the need to access identifiers.

Regardless of which UI the user may access patient data and/or the remote programming process through a common print application which is used for generation of medical device report(s). These reports consolidate current and historical, as well as objective and subjective data, into the single report. The report uses multiple display types: text fields, tabular data and data graphs.

This process facilitates tracking or "visualization" of the reprogramming process, describing the status of the reprogramming as it occurs, up to an indication of the successful completion of the reprogramming and annotation of the patient record with the updated status, in real-time via continuous interrogation.

The invention further comprises the following embodiments.

According to an embodiment of the present invention, a system is proposed comprising at least one medical device, a remote monitoring server (RMS) and at least one patient remote device (PR), wherein the PR is configured to establish a first bidirectional communication connection of the PR and the RMS and a second bidirectional communication connection of the PR and one chosen medical device, wherein the PR is further configured to (autonomously or user-driven) manage remote processes associated with the chosen medical device comprising remote interrogation of the chosen medical device and remote programming of the chosen medical device using the second bidirectional communication connection as well as data exchange with the RMS concerning interrogation data and/or program data with regard to the chosen medical device using the first bidirectional communication connection.

In an embodiment of the invention, the system further comprises at least one HCP remote device (CP), wherein the at least one CP is configured to establish a third bidirectional communication connection of the at least one CP and the RMS in order to provide additional real-time remote programming and/or interrogation of the chosen medical device using the at least one CP via the RMS and one PR corresponding to the chosen medical device.

In an embodiment of the present invention, the system is configured to maintain the first, second and/or third communication connections as continuous communication connections.

According to an embodiment of the invention, the system is configured such that the continuous communication connections are maintained until a "close" signal is sent from the one CP to the chosen medical device via the RMS and the corresponding PR and/or from one PR to the connected medical device and the RMS.

According to an embodiment of the invention, the at least one PR is a smartphone.

In an embodiment of the inventive system, at least one PR is configured to monitor and control incoming and outgoing communication data with regard to the second bidirectional communication connection.

Exemplarily, according to an embodiment, the least one PR provides a user interface platform configured to intervene and/or control the management of remote processes in the at least one PR by the patient and/or HCP.

In an embodiment of the present invention, the management of remote processes in the at least one PR comprises a validity check on a program for remote programming of the medical device.

In an embodiment of the inventive system, the at least one PR is configured to support video and/or audio call functionality simultaneously with displaying interrogation data of the medical device and/or to provide patient surveys, patient information push to the HCP and/or patient appointment requests.

In an embodiment of the present invention, at least one PR is configured to restrict and/or to prohibit pre-defined built-in functionality of the at least one PR.

In an embodiment of the inventive system, the RMS comprises a central repository of data collected by the at least one CP, the at least one PR and/or the at least one medical device.

In an embodiment of the present invention, each of the at least one CP, the RMS and at least one PR comprise a data buffer for communication and/or the at least one medical device is configured to adjust its data sampling rate based upon the bandwidth of communication with the PR.

According to an embodiment of the invention wherein the system comprises an authentication service which is configured to provide signed tokens to the at least one CP, wherein one signed token is valid for one particular remote programming session of the chosen medical device.

In an embodiment of the inventive system, wherein prior or during establishing the second communication connection between the RMS and the corresponding PR the RMS is configured to send a push notification to the corresponding PR thereby triggering this PR to poll the RMS at a faster rate.

In an embodiment of the present invention, for remote programming of the chosen medical device the CP is configured to produce a single program containing the updates and/or changes of the medical device's parameters and to transmit the single program to the medical device via the RMS and the corresponding PR. In an embodiment, the RMS is configured to encrypt the single program received from the CP, wherein the corresponding PR is configured to transmit the encrypted single program to the chosen medical device.

In an embodiment of the inventive system, the RMS is configured to be connected with a data warehouse and/or a clinical data warehouse, wherein the data warehouse and/or the clinical data warehouse are configured to import at least a part of the data stored in the central data repository. For instance, the RMS and/or the data warehouse and/or the clinical data warehouse are configured such that its respective data are accessible to external users depending on the access rights of the respective user.

In an embodiment of the present invention, the RMS is configured to store and/or manage the authentication and/or encryption keys and/or certificates for the at least one CP, at least one PR, at least one medical device as well as for the at least one user of the system, for example, patient, HCP and/or technician.

According to an embodiment of the invention, a method is proposed for programming and/or interrogation of one chosen medical device of a system comprising at least one medical device, a remote monitoring server (RMS) and at least one patient remote device (PR), wherein the PR establishes a first bidirectional communication connection of the PR and the RMS and a second bidirectional communication connection of the PR and one chosen medical device, wherein the PR further (autonomously or user-driven) manages remote processes associated with the chosen medical device comprising the remote interrogation of the chosen medical device and the remote programming of the chosen medical device using the second bidirectional communication connection as well as data exchange with the RMS concerning interrogation data and/or program data with regard to the chosen medical device using the first bidirectional communication connection. In an embodiment, the system further comprises at least one HCP remote device (CP), wherein the at least one CP establishes a third bidirectional communication connection of the at least one CP and the RMS in order to provide additional real-time remote programming and/or interrogation of the chosen medical device using the at least one CP via the RMS and one PR corresponding to the chosen medical device.

In an embodiment of the inventive method, the system maintains the first, second and/or third communication connections as continuous communication connections. Moreover, according to an embodiment, the system maintains the continuous communication connections until a close signal is sent from the one CP to the chosen medical device via the RMS and the corresponding PR and/or from one PR to the connected medical device and the RMS.

According to an embodiment of the inventive method, the at least one PR monitors and controls incoming and outgoing communication data with regard to the second bidirectional communication connection.

In an embodiment of the inventive method, the at least one PR provides a user interface platform which intervenes and/or controls the management of remote processes in the at least one PR by the patient and/or HCP.

According to an embodiment of the inventive method, the management of remote processes in the at least one PR comprises a validity check on a program for remote programming of the medical device.

In an embodiment of the inventive method, the management of remote processes in the at least one PR comprises a validity check on a program for remote programming of the medical device.

According to an embodiment of the inventive method, the at least one PR restricts and/or to prohibits pre-defined built-in functionality of the at least one PR.

In an embodiment of the inventive method, the RMS comprises a central repository of data collected by the at least one CP, the at least one PR and/or the at least one medical device.

According to an embodiment of the inventive method, each of the at least one CP, the RMS and at least one PR comprise a data buffer for communication and/or the at least one medical device is configured to adjust its data sampling rate based upon the bandwidth of communication with the PR.

In an embodiment of the inventive method, the system comprises an authentication service which provides signed tokens to the at least one CP, wherein one signed token is valid for one particular remote programming session of the chosen medical device.

According to an embodiment of the inventive method, prior or during establishing the second communication connection between the RMS and the corresponding PR the RMS sends a push notification to the corresponding PR thereby triggering this PR to poll the RMS at a faster rate.

In an embodiment of the inventive method, for remote programming of the chosen medical device the CP produces a single program containing the updates and/or changes of the medical device's parameters and transmits the single program to the medical device via the RMS and the corresponding PR. In an embodiment, the RMS encrypts the single program received from the CP, wherein the corresponding PR transmits the encrypted single program to the chosen medical device.

According to an embodiment of the inventive method, the RMS is connected with a data warehouse (210) and/or a clinical data warehouse, wherein the data warehouse and/or the clinical data warehouse import at least a part of the data stored in the central data repository.

According to an embodiment, the respective data of the RMS and/or the data warehouse and/or the clinical data warehouse are accessible to external users depending on the access rights of the respective user.

According to an embodiment of the inventive method, the RMS stores and/or manages the authentication and/or encryption keys and/or certificates for the at least one CP, at least one PR, at least one medical device as well as for the at least one user of the system, for example, patient, HCP and/or technician.

According to an embodiment of the present invention, a computer program product is proposed comprising instructions which, when executed by at least one processing unit, cause the at least one processing unit to perform the steps of the methods and embodiments of the methods disclosed. Moreover, a computer readable data carrier is disclosed for storing the computer program product according to the present invention.

The invention claimed is:

1. A system comprising at least one medical device (7), a remote monitoring server (RMS, 1) and at least one patient remote device (PR, 5), wherein the PR is configured to establish a first bidirectional communication connection (12, 14) of the PR and the RMS and a second bidirectional communication connection (13, 14) of the PR and one chosen medical device, wherein the PR is further configured to manage remote processes associated with the chosen medical device comprising remote interrogation of the chosen medical device and remote programming of the chosen medical device using the second bidirectional communication connection as well as data exchange with the RMS concerning interrogation data and/or program data with regard to the chosen medical device using the first bidirectional communication connection;

wherein the management of remote processes in the at least one PR (5) comprises a validity check on a program for remote programming of the medical device (7).

2. The system of claim 1, wherein the system further comprises at least one HCP remote device (CP, 3), wherein the at least one CP is configured to establish a third bidirectional communication connection (11, 14) of the at least one CP and the RMS (1) in order to provide additional real-time remote programming and/or interrogation of the chosen medical device using the at least one CP via the RMS and one PR (5) corresponding to the chosen medical device.

3. The system of claim 1, wherein the system is configured to maintain the first, second and/or third communication connections as continuous communication connections.

4. The system of claim 3, wherein the system is configured such that the continuous communication connections are maintained until a close signal is sent from the one CP (3) to the chosen medical device via the RMS (1) and the corresponding PR (5) and/or from one PR to the connected medical device and the RMS.

5. The system of claim 1, wherein the at least one PR (5) is a smartphone.

6. The system of claim 1, wherein the at least one PR (5) is configured to monitor and control incoming and outgoing communication data with regard to the second bidirectional communication connection.

7. The system of claim 1, wherein the at least one PR (5) provides a user interface platform configured to intervene and/or control the management of remote processes in the at least one PR by the patient and/or HCP.

8. The system of claim 1, wherein the validity check on the program for remote programming of the medical device (7) comprises a check that a required number of electrodes is defined for the program.

9. The system of claim 1, wherein the at least one PR (5) is configured to support video and/or audio call functionality simultaneously with displaying interrogation data of the medical device (7) and/or to provide patient surveys, patient information push to the HCP and/or patient appointment requests and/or wherein the at least one PR is configured to restrict and/or to prohibit pre-defined built-in functionality of the at least one PR.

10. The system of claim 1, wherein prior or during establishing the second communication connection between the RMS (1) and the corresponding PR (5) the RMS is configured to send a push notification to the corresponding PR thereby triggering this PR to poll the RMS at a faster rate.

11. The system of claim 1, wherein for remote programming of the chosen medical device the CP (3) is configured to produce a single program containing the updates and/or changes of the medical device's parameters and to transmit the single program to the medical device via the RMS (1) and the corresponding PR, wherein the RMS is configured to encrypt the single program received from the CP, wherein the corresponding PR (5) is configured to transmit the encrypted single program to the chosen medical device.

12. A method for programming and/or interrogation of one chosen medical device of a system comprising at least one medical device (7), a remote monitoring server (RMS, 1) and at least one patient remote device (PR, 5), wherein the PR establishes a first bidirectional communication connection (12, 14) of the PR and the RMS and a second bidirectional communication connection (13, 14) of the PR and one chosen medical device, wherein the PR further manages remote processes associated with the chosen medical device comprising the remote interrogation of the chosen medical device and the remote programming of the chosen medical device using the second bidirectional communication connection as well as data exchange with the RMS concerning interrogation data and/or program data with regard to the chosen medical device using the first bidirectional communication connection;
wherein the system further comprises at least one HCP remote device (CP, 3), wherein the at least one CP establishes a third bidirectional communication connection (11, 14) of the at least one CP and the RMS (1) in order to provide additional real-time remote programming and/or interrogation of the chosen medical device using the at least one CP via the RMS and one PR (5) corresponding to the chosen medical device.

13. The method of claim 12, wherein the least one CP is enabled to communicate with the chosen medical device only indirectly via a communication path comprising the first, second and third bidirectional connections.

14. A non-transitory computer readable medium storing a computer program product comprising instructions which, when executed by at least one processing unit, cause the at least one processing unit to perform the steps of the method according to claim 12.

15. A computer comprising a processor and the non-transitory computer readable medium storing the computer program product according to claim 14.

* * * * *